US010507338B2

(12) United States Patent
Kuwahara et al.

(10) Patent No.: US 10,507,338 B2
(45) Date of Patent: Dec. 17, 2019

(54) PARTICLE BEAM RADIOTHERAPY SYSTEM

(71) Applicant: Toshiba Medical Systems Corporation, Otawara-shi (JP)

(72) Inventors: Takayuki Kuwahara, Otawara (JP); Satoru Ohishi, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/793,047

(22) Filed: Oct. 25, 2017

(65) Prior Publication Data

US 2018/0117360 A1 May 3, 2018

(30) Foreign Application Priority Data

Oct. 31, 2016 (JP) ................................ 2016-213341
Oct. 12, 2017 (JP) ................................ 2017-198505

(51) Int. Cl.
*A61N 5/10* (2006.01)
*G21K 1/08* (2006.01)

(52) U.S. Cl.
CPC ......... *A61N 5/1049* (2013.01); *A61N 5/1043* (2013.01); *G21K 1/08* (2013.01); *A61N 5/103* (2013.01); *A61N 5/1081* (2013.01); *A61N 2005/1058* (2013.01); *A61N 2005/1087* (2013.01)

(58) Field of Classification Search
USPC ...................................................... 250/505.1
See application file for complete search history.

(56) References Cited

U.S. PATENT DOCUMENTS 8,319,198 B2 * 11/2012 Bert .................... A61N 5/1043 250/492.3
8,405,050 B2 * 3/2013 Bert ...................... A61N 5/103 250/491.1
2013/0114792 A1 * 5/2013 Zilberstein ........... G01T 1/1611 378/62
2015/0306423 A1 10/2015 Bharat et al.

FOREIGN PATENT DOCUMENTS

JP 2006-158678 6/2006
JP 2015-205110 11/2015
JP 2015-536783 12/2015

OTHER PUBLICATIONS

S. Nishio, "Importance of nuclear reaction in proton cancer cancer treatment", RCNP research group 2012, Sep. 28-29, 2012, 10 pages (with English translation).

* cited by examiner

*Primary Examiner* — Phillip A Johnston
(74) *Attorney, Agent, or Firm* — Oblon, McClelland, Maier & Neustadt, L.L.P.

(57) ABSTRACT

A gantry applies particle beams to a subject. An ultrasonic diagnostic apparatus scans the subject with ultrasonic waves via an ultrasonic probe, and acquires an ultrasonic image concerning a radiotherapy target region of the subject. A processing circuitry specifies a first planned point of a Bragg peak in the ultrasonic image, which anatomically coincides approximately with a second planned point of the Bragg peak decided in radiotherapy planning. The processing circuitry estimates a sighting point of the Bragg peak of a particle beam based on a body surface position of the subject and an actual range of the particle beam. The display displays the ultrasonic image to indicate the first planned point and the sighting point.

17 Claims, 12 Drawing Sheets

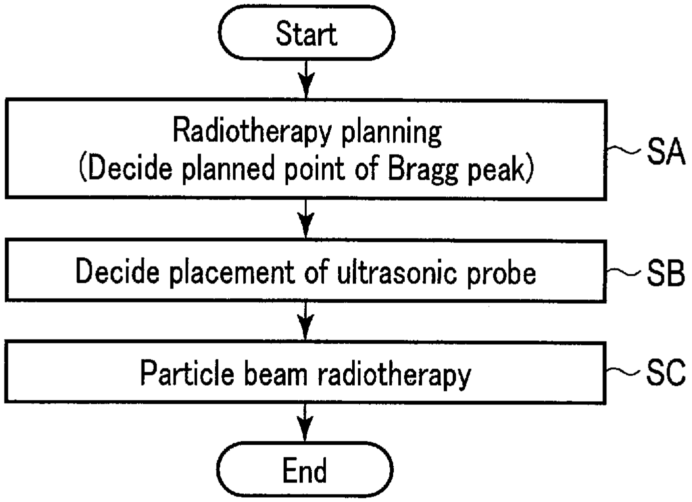
F I G. 3
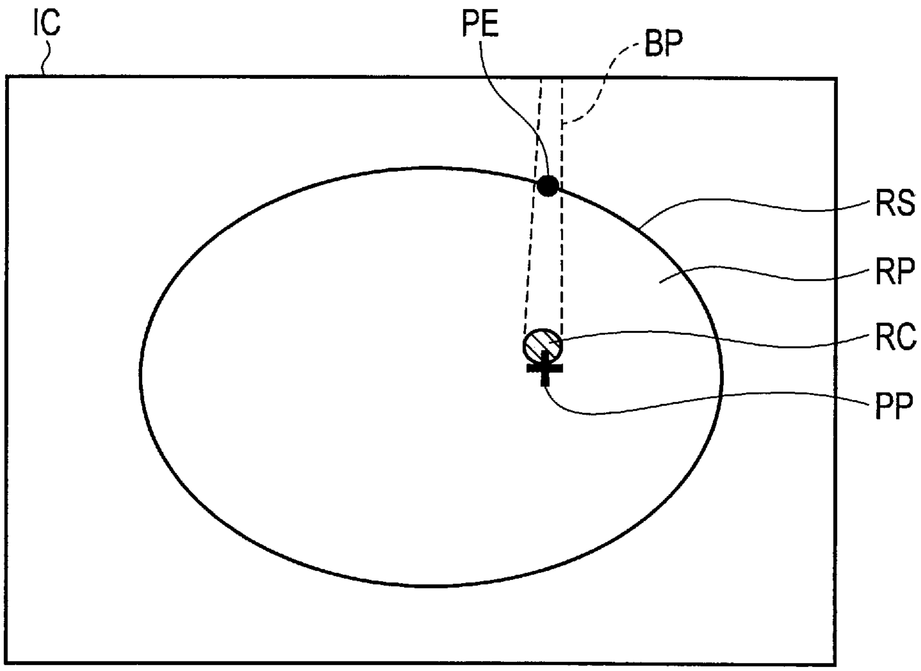
F I G. 4

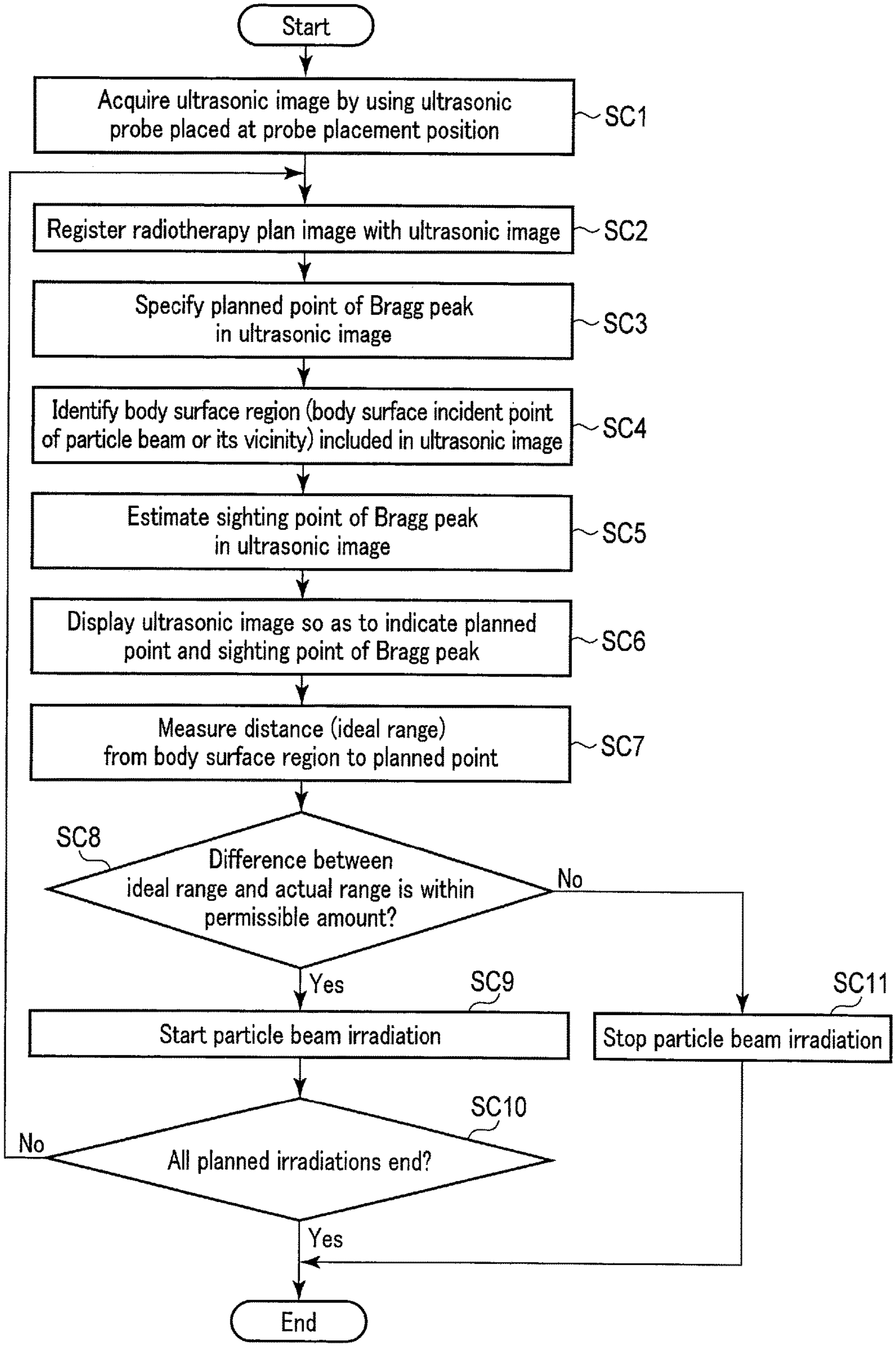
F I G. 6

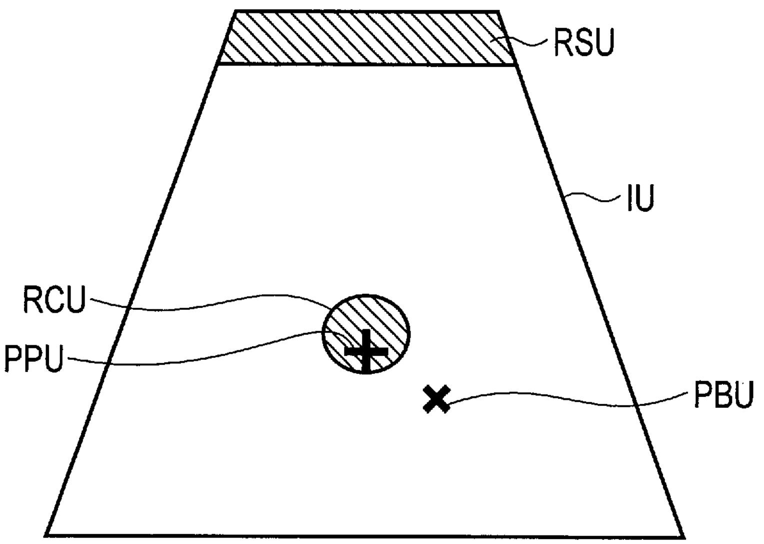
F I G. 9
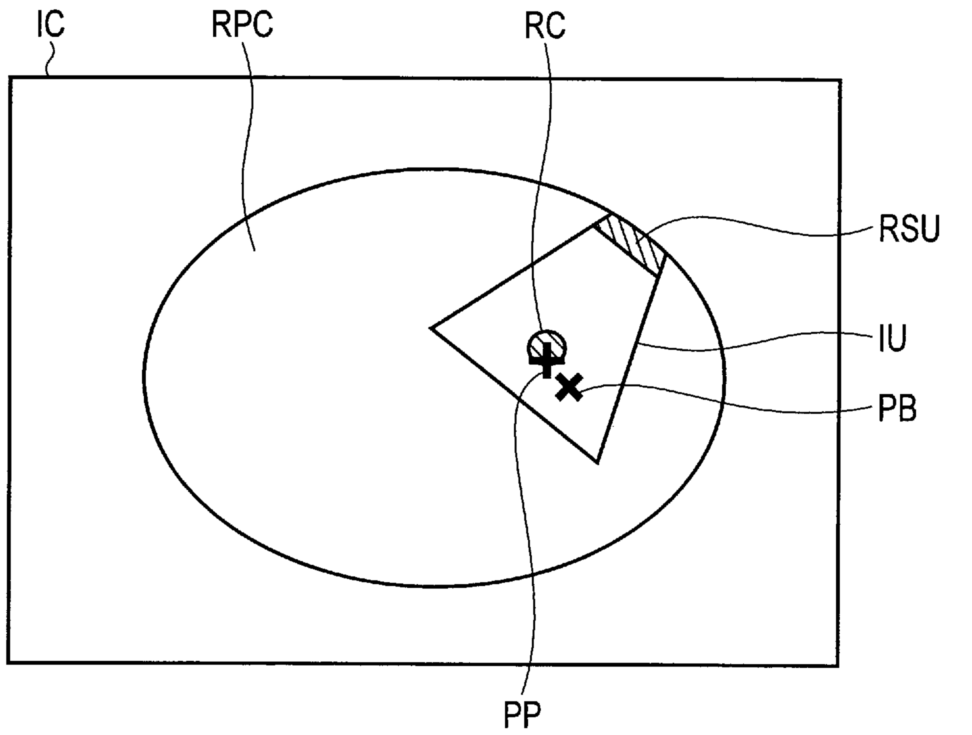
F I G. 10

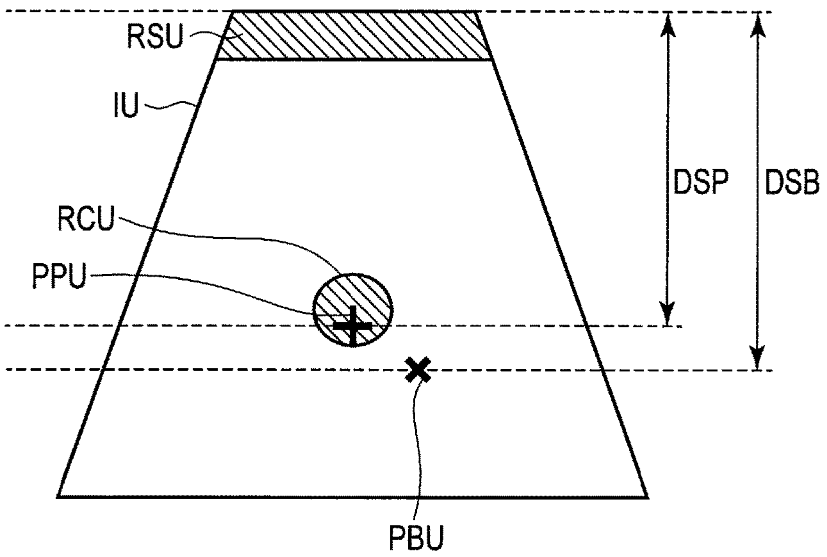
F I G. 11
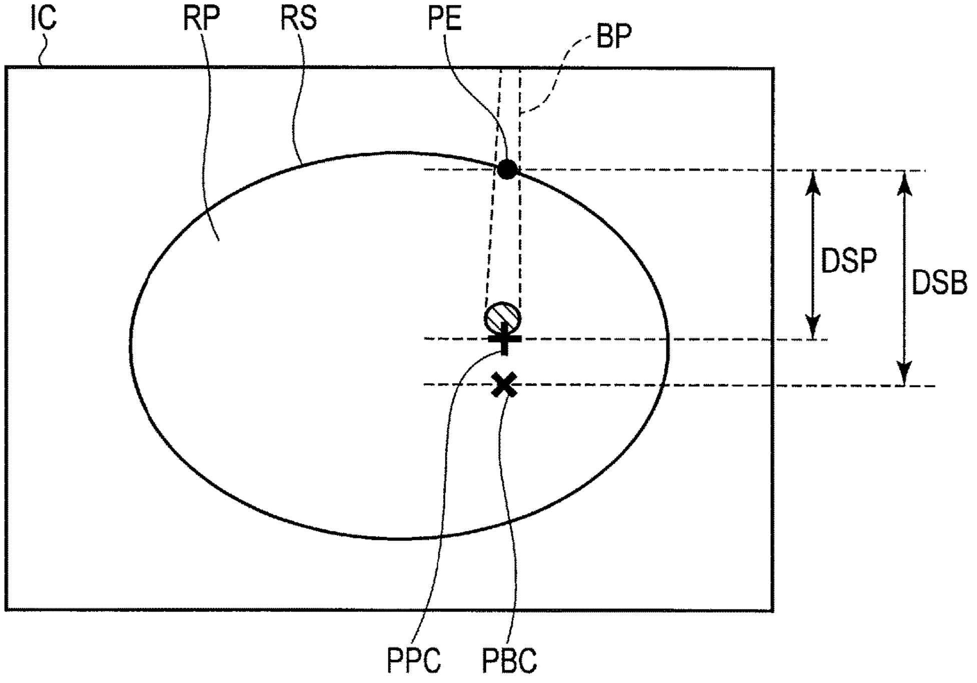
F I G. 12

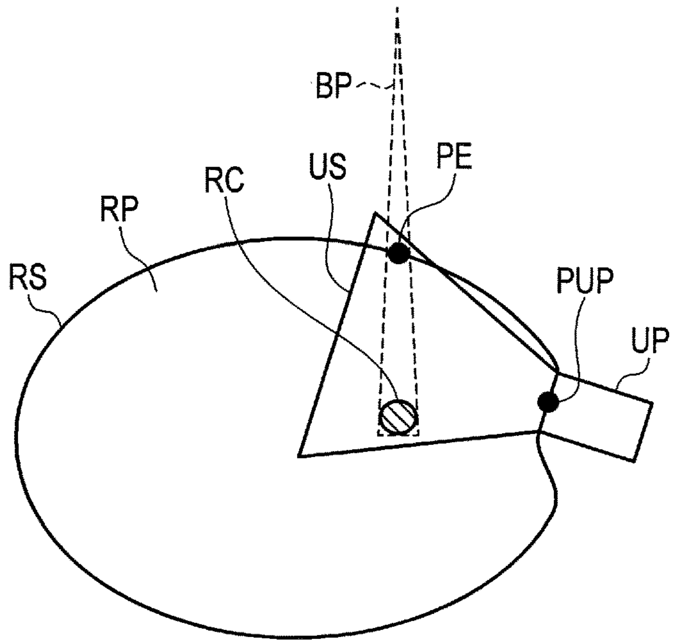
F I G. 13
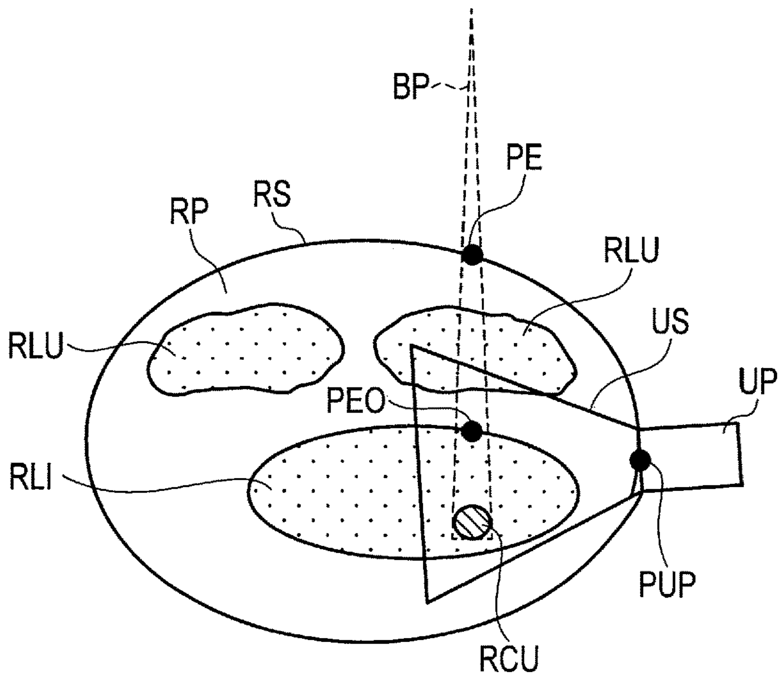
F I G. 14

| Differential value | Energy modulation value |
|---|---|
| −10mm | +1Mev |
| ⋮ | ⋮ |
| −1mm | +0.3MeV |
| +1mm | −0.3MeV |
| ⋮ | ⋮ |
| +10mm | −1MeV |
F I G. 16
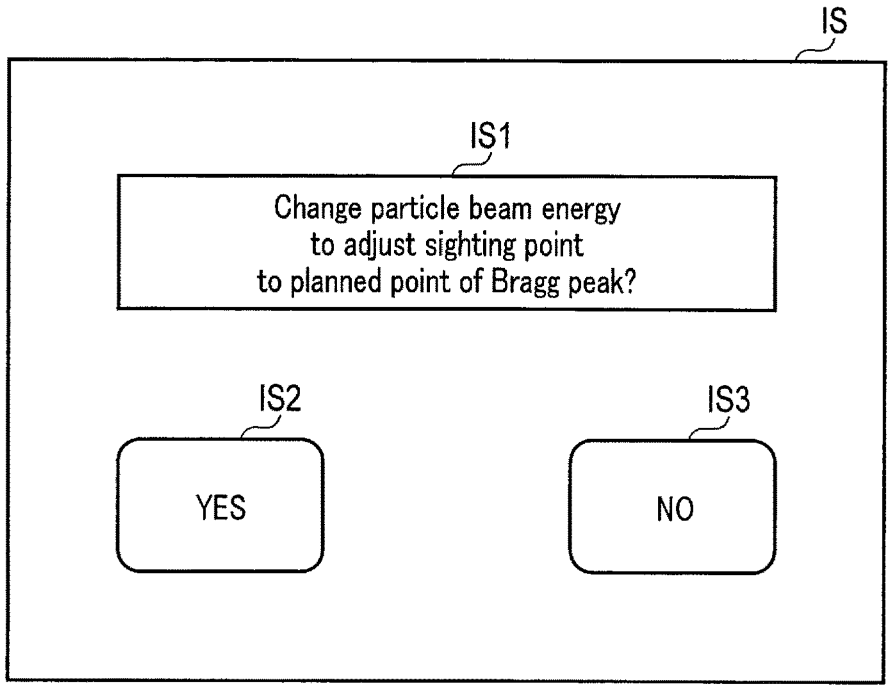
F I G. 17

PARTICLE BEAM RADIOTHERAPY SYSTEM

CROSS-REFERENCE TO RELATED APPLICATIONS

This application is based upon and claims the benefit of priority from the prior Japanese Patent Application No. 2016-213341, filed Oct. 31, 2016 and the prior Japanese Patent Application No. 2017-198505, filed Oct. 12, 2017, the entire contents of all of which are incorporated herein by reference.

FIELD

Embodiments described herein relate generally to a particle beam radiotherapy system.

BACKGROUND

In particle beam radiotherapy, it is important that a sight of a Bragg peak is set right on a tumor as planned. When the position of the tumor fluctuates due to the body motion, etc., a Bragg peak sight will be set at a position different from the planned position. As a method for confirming a sighting point of a Bragg peak, there is a method for detecting, by an electron particle track detecting-type Compton camera, gamma rays generated when particles collide with a living body. However, this is a large-scale, and requires an expensive electron particle track detecting-type Compton camera.

BRIEF DESCRIPTION OF THE DRAWING

FIG. 3 is a flowchart showing a perspective procedure of the particle beam radiotherapy system in FIG. 1.

FIG. 4 is a view showing an example of a CT image onto which radiotherapy plan information generated in step SA in FIG. 3 is superimposed.

FIG. 6 is a flowchart showing a procedure of the particle beam radiotherapy system in step SC in FIG. 3.

FIG. 9 is a view showing an example of an ultrasonic image clearly indicating a planned point and a sighting point of Bragg peak, which is displayed by display circuitry in step SC6 in FIG. 6.

FIG. 10 is a view showing a superimposed image of the ultrasonic image clearly indicating the planned point and the sighting point of the Bragg peak and the radiotherapy plan CT image, which is displayed by the display circuitry in step SC6 in FIG. 6.

FIG. 11 is a view showing an ideal range and an actual range in the ultrasonic image according to steps SC7 and SC8 in FIG. 6.

FIG. 12 is a view showing an ideal range and an actual range in the radiotherapy plan CT image according to steps SC7 and SC8 in FIG. 6.

FIG. 13 is a view showing the placement of the ultrasonic probe decided by another method in step SB in FIG. 3.

FIG. 14 is a view showing the placement of the ultrasonic probe decided by another method in step SB in FIG. 3.

FIG. 16 is a view showing an example of a difference/modulation value table used in step SD9 in FIG. 15.

FIG. 17 is a view showing an example of an inquiry screen displayed in step SD10 in FIG. 15.

DETAILED DESCRIPTION

A particle beam radiotherapy system according to this embodiment includes a gantry, an ultrasonic diagnostic apparatus, processing circuitry, and display. The gantry applies particle beams to a subject. The ultrasonic diagnostic apparatus scans the subject with ultrasonic waves via an ultrasonic probe, and acquires an ultrasonic image concerning a radiotherapy target region of the subject. The processing circuitry specifies a first planned point of a Bragg peak in the ultrasonic image, which anatomically coincides approximately with a second planned point of the Bragg peak decided in radiotherapy planning. The processing circuitry estimates a sighting point of the Bragg peak of a particle beam applied by a radiation head based on information concerning a body surface position of the subject and an actual range of the particle beam applied by the radiation head. The display displays the ultrasonic image so as to indicate the first planned point and the sighting point.

Hereinafter, the particle beam radiotherapy system according to this embodiment will be described below with reference to the accompanying drawings.

Figure 1:
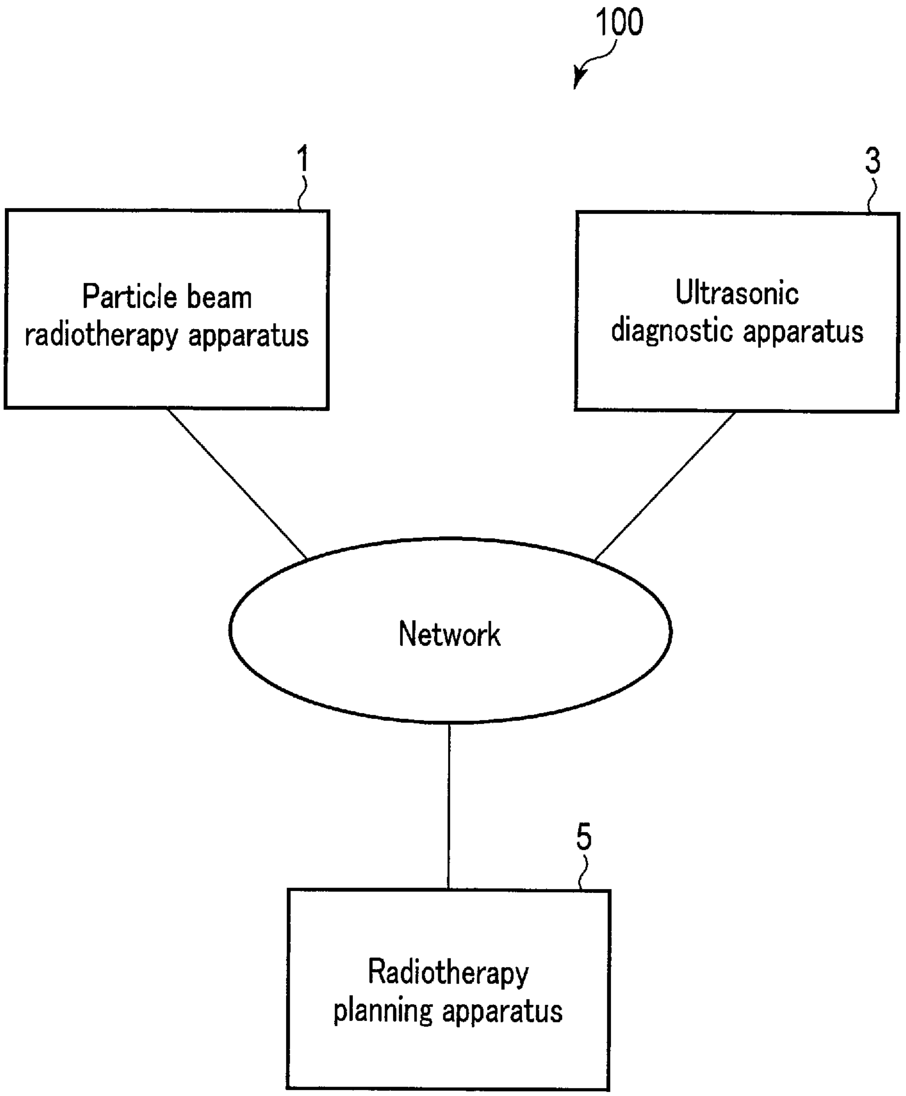
FIG. 1 is a block diagram showing the arrangement of a particle beam radiotherapy system according to an embodiment.

FIG. 1 shows the arrangement of a particle beam radiotherapy system 100 according to this embodiment. As shown in FIG. 1, the particle beam radiotherapy system 100 according to this embodiment includes a particle beam radiotherapy apparatus 1, an ultrasonic diagnostic apparatus 3, and a radiotherapy planning apparatus 5, which are connected so as to be mutually communicable via a network, etc.

The ultrasonic diagnostic apparatus 3 includes an ultrasonic probe and a console. The ultrasonic probe transmits/receives ultrasonic waves. The console scans a subject with ultrasonic waves via the ultrasonic probe in the particle beam radiotherapy by the particle beam radiotherapy apparatus 1, and acquires an ultrasonic image targeted for a radiotherapy target region of the subject. In this embodiment, a radiotherapy target region may be any region which can be treated by particle beams; hereinafter, it is assumed that the radiotherapy target region is a tumor. The acquired ultrasonic image is transmitted to the particle beam radiotherapy apparatus 1. The ultrasonic image according to this embodiment may be a two-dimensional image comprising a plurality of pixels arranged two-dimensionally, or may be a three-dimensional image comprising a plurality of voxels arranged three-dimensionally.

The radiotherapy planning apparatus 5 is, for example, a generic computer or a work station. The radiotherapy planning apparatus 5 produces a radiotherapy plan of particle beam radiotherapy by the particle beam radiotherapy apparatus 1 based on a radiotherapy plan image acquired in advance in the radiotherapy planning. Specifically, the radiotherapy planning apparatus 5 decides a dose distribution and a planned point of the Bragg peak, an irradiation direction of the particle beam, a beam path of the particle beam, a body surface incident point of the particle beam, etc. The dose distribution is a spatial distribution of a radiation dose of the particle beam to be applied by particle beam radiotherapy. The planned point of the Bragg peak is an anatomical position on which a Bragg peak sight is set. The irradiation direction of the particle beam is a direction to apply the particle beam. The beam path of the particle beam is a transmission path of the particle beam. The body surface incident point of the particle beam is a position where the particle beam is made incident into a body surface of the subject. The radiotherapy plan image is acquired by a medical image diagnostic apparatus, such as an X-ray computed tomography apparatus, a magnetic resonance imaging apparatus, and an X-ray diagnostic apparatus. The acquired radiotherapy plan image is transmitted to the particle beam radiotherapy apparatus 1. The radiotherapy plan image according to this embodiment may be a two-dimensional image comprising a plurality of pixels arranged two-dimensionally, or may be a three-dimensional image comprising a plurality of voxels arranged three-dimensionally.

The particle beam radiotherapy apparatus 1 applies particle beams to a tumor of the subject in accordance with the radiotherapy plan produced by the radiotherapy planning apparatus 5. In the particle beam radiotherapy, the particle beam radiotherapy apparatus 1 immediately estimates a sighting point of the Bragg peak of the particle beam by using the ultrasonic image acquired by the ultrasonic diagnostic apparatus 3. Note that the sighting point according to this embodiment corresponds to a position on which a sight of the Bragg peak of the particle beam being applied or to be applied in the particle beam radiotherapy is set.

Figure 2:
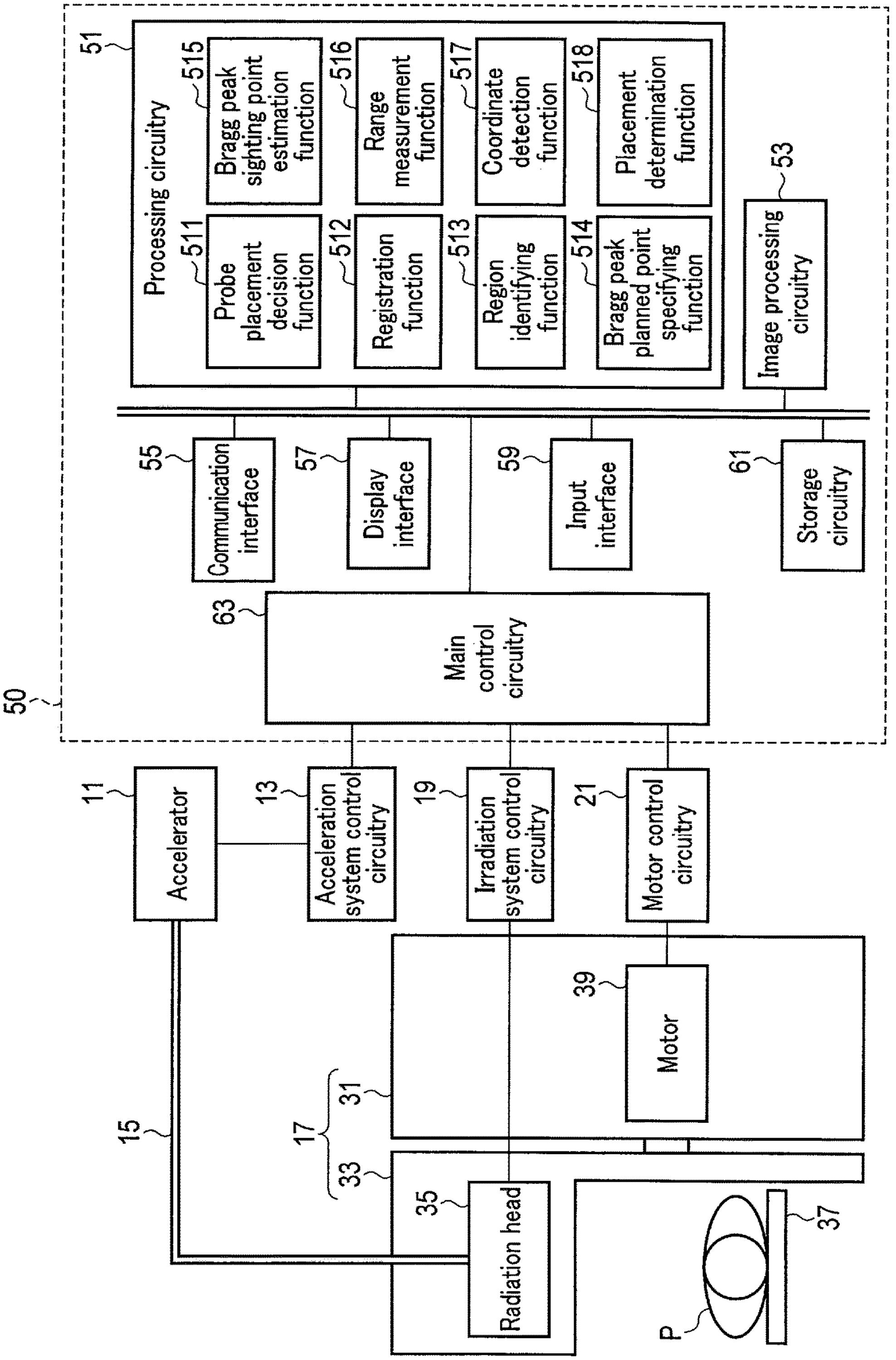
FIG. 2 is a block diagram showing the arrangement of a particle beam radiotherapy apparatus in FIG. 1.

FIG. 2 shows the arrangement of the particle beam radiotherapy apparatus 1 in FIG. 1. As shown in FIG. 2, the particle beam radiotherapy apparatus 1 includes an accelerator 11, acceleration system control circuitry 13, a transport system 15, a gantry 17, a bed 37, irradiation system control circuitry 19, motor control circuitry 21, and a console 50.

The accelerator 11 generates particle beams by accelerating heavy-ions, protons, or the like generated by an ion source, etc. by using a linear accelerator 11, a circular accelerator 11, etc. The acceleration system control circuitry 13 controls the accelerator 11 in accordance with a command from main control circuitry 63 of the console 50. The transport system 15 is a transport path for transporting the particle beam exiting from the accelerator 11 to the gantry 17.

The gantry 17 includes a fixed portion 31 and a rotating portion 33. The fixed portion 31 is installed on the floor surface and supports the rotating portion 33 so as to allow it to rotate about a rotation axis. A radiation head 35 is attached to the rotating portion 33. The radiation head 35 applies the particle beam transported by the transport system 15 to the subject P placed on a bed with the particle beam. The radiation head 35 is equipped with a collimator (not shown), such as a multileaf collimator, and can form a particle beam in conformity with the shape of an irradiation region. The radiation head 35 has an electromagnetic deflecting plate for deflection in a lateral direction and an electromagnetic deflecting plate for deflection in a longitudinal direction (not shown). Note that the lateral direction coincides with the rotating direction of the rotating portion 33, and the longitudinal direction is perpendicular to the lateral direction. The irradiation system control circuitry 19 drives the electromagnetic deflecting plates and the collimator in accordance with the command from the main control circuitry 63 of the console 50 to apply a particle beam to the subject P in conformity with the radiotherapy plan. The irradiation system control circuitry 19, to be described below, switches between irradiation and a stoppage of the irradiation of the particle beam in accordance with the position of the sighting point of the Bragg peak estimated by the processing circuitry 51. The rotating portion 33 is provided with a projector (not shown) for irradiating to the subject P a visible light indicating an irradiation region of the particle beam.

Figure 7:
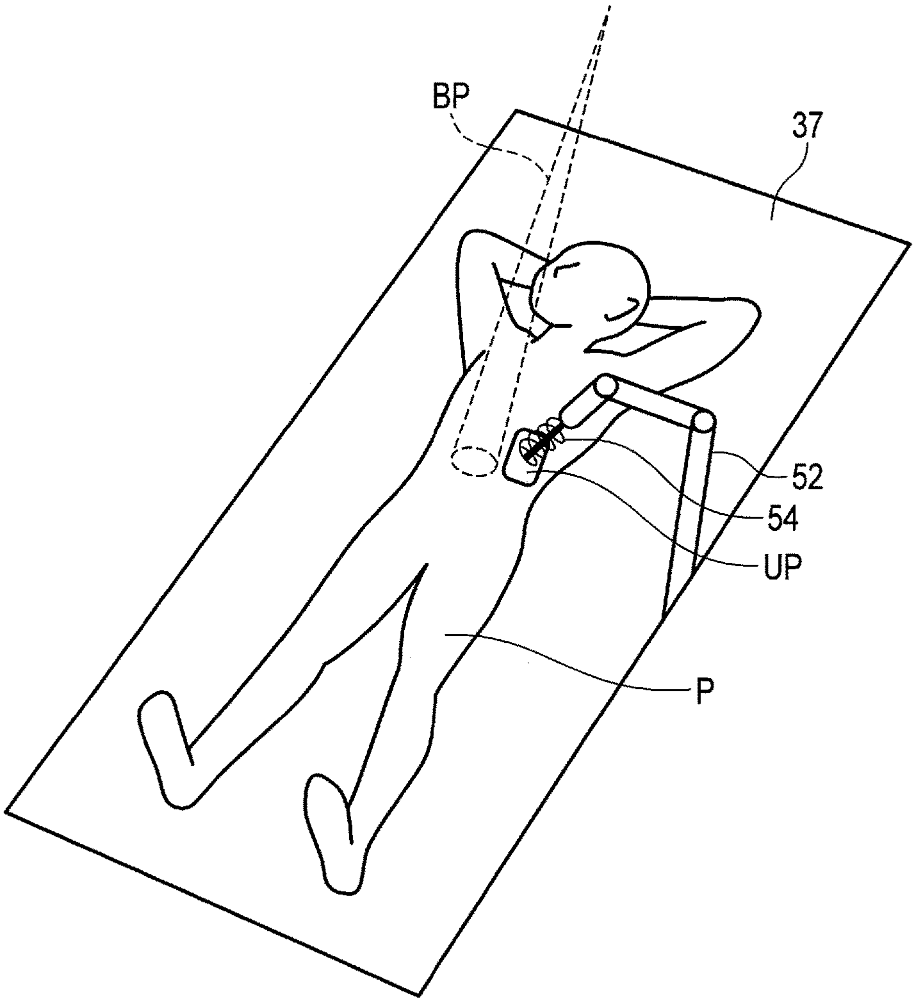
FIG. 7 is a view showing an overview surrounding a subject in the particle beam radiotherapy in FIG. 6.

As shown in FIG. 7, an ultrasonic probe UP of the ultrasonic diagnostic apparatus 3 is attached to the bed 37 via an arm 52. Namely, one end of the arm 52 is fixed to the bed 37. The other end of the arm 52 has an arrangement for holding the ultrasonic probe UP as well as pressing the ultrasonic probe UP on the body surface of the subject P. Specifically, the arm 52 includes an elastic body 54, such as a spring, as a mechanism for holding the ultrasonic probe UP. By including the elastic body 54, the arm 52 allows the motion of the ultrasonic probe UP along with respiration, etc. of the subject P as well as presses the ultrasonic probe UP on the subject P with appropriate power.

Hereinafter, the arm 52 will be explained as being positioned manually by a medical practitioner, such as a technologist, but may be positioned automatically in accordance with an input, etc. from the console 50.

As shown in FIG. 2, a motor 39 is incorporated in the fixed portion 31. The motor 39 generates a motive power for allowing the fixed portion 31 to rotate the rotating portion 33. The motor control circuitry 21 drives the motor 39 in accordance with the command from the main control circuitry 63 of the console 50 to place the radiation head 35 at a predetermined rotation angle.

As shown in FIG. 2, the console 50 includes processing circuitry 51, image processing circuitry 53, communication interface 55, display 57, input interface 59, storage circuitry 61, and main control circuitry 63. The processing circuitry 51, the image processing circuitry 53, the communication interface 55, the display 57, the input interface 59, the storage circuitry 61, and the main control circuitry 63 are connected so as to be mutually communicable via a bus.

The processing circuitry 51 includes a processor, such as a CPU (Central Processing Unit) and a GPU (Graphics Processing Unit), and a memory, such as a ROM (Read Only Memory) and a RAM (Random Access Memory), as hardware resources. Specifically, the processing circuitry 51 includes a probe placement decision function 511, a registration function 512, a region identifying function 513, a Bragg peak planned point specifying function 514, a Bragg peak sighting point estimation function 515, a range measurement function 516, a coordinate detection function 517, and a placement determination function 518. The image processing circuitry 53 may be implemented by an ASIC (Application Specific Integrated Circuit), FPGA (Field Programmable Gate Array), CPLD (Complex Programmable Logic Device), or SPLD (Simple Programmable Logic Device) which can implement the above functions.

In the probe placement decision function 511, the processing circuitry 51 decides the placement of the ultrasonic probe for acquiring the ultrasonic image by the ultrasonic diagnostic apparatus 3 in the particle beam radiotherapy, based on the irradiation direction of the particle beam applied from the radiation head 35.

In the registration function 512, the processing circuitry 51 registers the ultrasonic image acquired by the ultrasonic diagnostic apparatus 3 with the radiotherapy plan image by image processing.

In the region identifying function 513, the processing circuitry 51 identifies a specific image region included in the ultrasonic image and the radiotherapy plan image by image processing. As a specific image region, for example, there is an image region (to be referred to as a tumor region hereinafter) concerning the radiotherapy target tumor included in the subject P, and an image region (to be referred to as a body surface region hereinafter) concerning the body surface of the subject P.

In the Bragg peak planned point specifying function 514, the processing circuitry 51 specifies a planned point of the Bragg peak in the ultrasonic image, which anatomically coincides approximately with the planned point of the Bragg peak decided by the radiotherapy planning apparatus 5, etc. in the radiotherapy planning.

In the Bragg peak sighting point estimation function 515, the processing circuitry 51 estimates a sighting point of the Bragg peak of the particle beam applied by the radiation head 35 in the particle beam radiotherapy, based on information (to be referred to as body surface information hereinafter) concerning the body surface position of the subject and an actual range applied by the radiation head 35 in the particle beam radiotherapy. The sighting point of the Bragg peak according to this embodiment is an anatomical point on which the sight of the Bragg peak is actually set in the particle beam radiotherapy. The body surface information of the subject may be a body surface region identified by the region identifying function 513, and may be coordinates of the body surface of the subject defined by a real-space coordinate system. The coordinates of the body surface of the subject defined by the real-space coordinate system are, for example, measured by a sensor to be described below.

In the range measurement function 516, the processing circuitry 51 measures a distance from the body surface region of the subject P included in the ultrasonic image and the radiotherapy plan image to the sighting point of the Bragg peak estimated by the Bragg peak sighting point estimation function 515. The measured distance corresponds to an ideal range.

In the coordinate detection function 517, the processing circuitry 51 detects coordinates in the real coordinate system of the point specified in the ultrasonic image or the radiotherapy plan image, based on an output signal from a position sensor.

In the placement determination function 518, the processing circuitry 51 determines whether an actual placement of the ultrasonic probe UP is appropriate or not, based on the placement of the ultrasonic probe UP decided by the probe placement decision function 511.

The image processing circuitry 53 includes a processor, such as a CPU and a GPU, and a memory, such as a ROM and a RAM, as hardware resources. The image processing circuitry 53 applies various types of image processing to radiotherapy plan images. For example, the image processing circuitry 53 applies three-dimensional image processing, such as volume rendering, surface volume rendering, pixel value projection processing, MPR (Multi-Planer Reconstruction) processing, or CPR (Curved MPR) processing, to three-dimensional radiotherapy plan images, and thereby generates two-dimensional medical images for display. The image processing circuitry 53 may be implemented as an ASIC, an FPGA, a CPLD, or an SPLD which can implement the above image processing.

The communication interface 55 performs data communication between the ultrasonic diagnostic apparatus 3 and the radiotherapy planning apparatus 5, which constitute the particle beam radiotherapy system 100, via a wired or wireless means (not shown).

The display 57 displays various types of information. Specifically, the display 57 connected a display interface. The display interface converts data representing a display target into a video signal. A display signal is supplied to the display 57. The display 57 displays the video signal representing the display target. As a display 57, it is possible to use, for example, a CRT display, a liquid crystal display, an organic EL display, an LED display, a plasma display, or a given display known in this technical field, as appropriate.

The input interface 59 is connected to an input device. The input device accepts various types of commands from a user. As input devices, it is possible to use a keyboard, a mouse, various types of switches, etc. The input interface 59 supplies output signals from the input device to the main control circuitry 63 via a bus.

The storage circuitry 61 is a storage, such as an HDD (Hard Disk Drive), an SSD (Solid State Drive), or an integrated circuit storage, which stores various types of information. For example, the storage circuitry 61 stores the radiotherapy plan information and the radiotherapy plan image supplied from the radiotherapy planning apparatus 5. In addition, the storage circuitry 61 stores the ultrasonic image supplied from the ultrasonic diagnostic apparatus 3. As hardware, the storage circuitry 61 may be a drive assembly or the like which reads and writes various types of information from and to portable storage media, such as a CD-ROM drive, a DVD drive, and a flash memory.

The main control circuitry 63 functions as the main unit of the particle beam radiotherapy apparatus 1. The main control circuitry 63 performs the particle beam radiotherapy according to this embodiment by executing an operation program according to this embodiment stored in the storage circuitry 61, etc. to control each portion in accordance with the operation program.

An example of the operation of the particle beam radiotherapy system 100 according to this embodiment will be described below.

FIG. 3 shows a perspective procedure of the particle beam radiotherapy system 100 according to this embodiment. As shown in FIG. 3, first of all, the radiotherapy planning apparatus 5 executes a radiotherapy plan concerning the radiotherapy target subject P (step SA). In step SA, the radiotherapy planning apparatus 5 produces the radiotherapy plan by using the radiotherapy plan image acquired by the medical image diagnostic apparatus in advance to generate radiotherapy plan information. As radiotherapy plan information, for example, there are a dose distribution and a planned point of the Bragg peak, an irradiation direction of the particle beam, a beam path of the particle beam, a body surface incident point of the particle beam, and an actual range. In the following embodiment, it is assumed that the radiotherapy plan image is a CT image acquired by an X-ray computed tomography apparatus. Hereinafter, a CT image to be used for radiotherapy planning will be generically termed a radiotherapy plan CT image. Typically, the radiotherapy plan CT image is a three-dimensional image defined by an orthogonal three-dimensional coordinate system.

FIG. 4 shows an example of a radiotherapy plan CT image IC onto which radiotherapy plan information is superimposed. As shown in FIG. 4, the radiotherapy plan CT image IC includes an image region (to be referred to as a subject region hereinafter) RP concerning the subject P. An edge portion of the subject region RP is defined by an image region (to be referred to as a body surface region hereinafter) RS concerning the body surface of the subject P. The body surface region RS is, for example, extracted by image processing performed by the radiotherapy planning apparatus 5. The subject region RP includes a radiotherapy target region RC which is an image region concerning the radiotherapy target. Hereinafter, an explanation will be given assuming that the radiotherapy target is a tumor, and the radiotherapy target region RC will be termed a tumor region RC. The tumor region RC is, for example, extracted by image processing performed by the radiotherapy planning apparatus 5. A beam path BP of the particle beam in the particle beam radiotherapy is set so as to pass through the tumor region RC. An angle around a reference axis of the beam path BP is defined by the irradiation direction. The reference axis can be discretionarily set. In the particle beam radiotherapy, the reference axis is positioned at a rotation axis of the gantry 17 of the particle beam radiotherapy apparatus 1. The beam path BP is manually set by the user via the input device, etc., or automatically set by image processing. A crossing point of the beam path BP and the edge portion (body surface region) of the subject region RP is defined as an incident point PE. A planned point PP of the Bragg peak is set in the tumor region RC by the radiotherapy planning apparatus 5. The planned point PP is manually set by the user via the input device, etc., or is automatically set by image processing. A distance from the incident point PE to the planned point PP is set as an actual range. The actual range is equal to a range actually observed in the particle beam radiotherapy. This is because, while a range changes in accordance with energy of a particle beam, the energy of the particle beam in the particle beam radiotherapy is decided based on the range decided in the radiotherapy plan. The radiotherapy plan information and the radiotherapy plan CT image IC are transmitted to the particle beam radiotherapy apparatus 1 by the radiotherapy planning apparatus 5.

Upon executing step SA, the particle beam radiotherapy apparatus 1 executes processing for deciding the placement of the ultrasonic probe (step SB). In step SB, the processing circuitry 51 of the particle beam radiotherapy apparatus 1 executes the probe placement decision function 511. In the probe placement decision function 511, the processing circuitry 51 decides the placement of the ultrasonic probe for acquiring the ultrasonic image by the ultrasonic diagnostic apparatus 3 in the particle beam radiotherapy, based on the irradiation direction of the particle beam. The irradiation direction of the particle beam is set in the radiotherapy plan CT image by the radiotherapy planning apparatus 5 in step SA. The processing circuitry 51 decides, for example, the placement of the ultrasonic probe by using the radiotherapy plan CT image. The image processing circuitry 53 generates a rendering image applied to the ultrasonic probe placement decision by applying three-dimensional image processing to the radiotherapy plan CT image. As a method for deciding the placement, for example, the following method is available.

Figure 5:
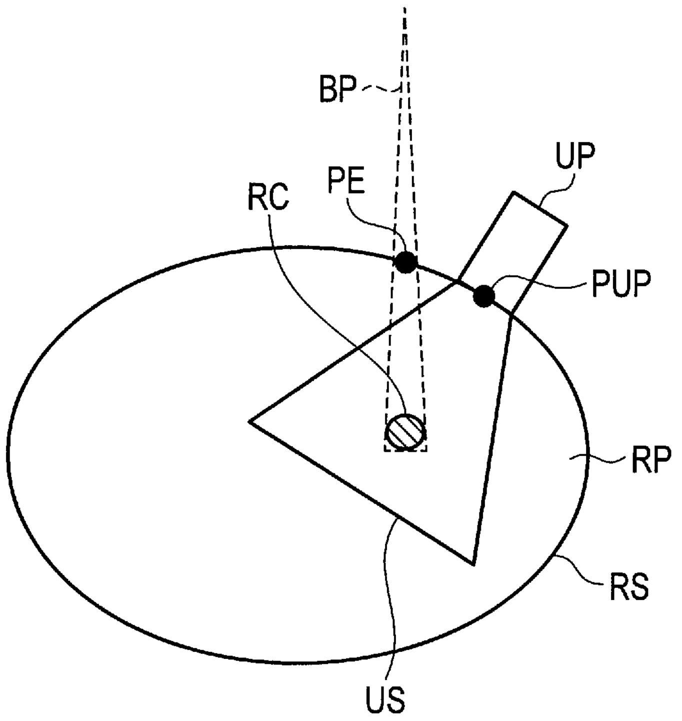
FIG. 5 is a view showing the placement of an ultrasonic probe decided in step SB in FIG. 3.

FIG. 5 shows the placement of the ultrasonic probe UP decided in step SB. As shown in FIG. 5, the radiotherapy plan CT image includes the subject region RP defined by the body surface region RS. The subject region RP includes the tumor region RC. The beam path BP is set so as to pass through the tumor region RC, and the incident point PE is set at a crossing point of the body surface region RS and the beam path BP. The radiotherapy plan CT image used for the ultrasonic probe UP placement decision may be any kinds of rendering images, such as an MPR image and a volume rendering image. In FIG. 5, it is assumed that the radiotherapy plan CT image is, as an example, an MPR image concerning an axial section.

As shown in FIG. 5, the processing circuitry 51 decides the placement of the ultrasonic probe UP so that an ultrasonic scanning region US can include the tumor region RC. The incident point PE is not included in the ultrasonic scanning region US. The placement is defined by a position and an angle of the ultrasonic probe UP. The position and the angle of the ultrasonic probe UP are, for example, defined in a three-dimensional image coordinate system of the radiotherapy plan CT image. In more detail, a position PUP of the ultrasonic probe UP is decided at a position where the ultrasonic scanning region US can include the tumor region RC and is in the proximity of the incident point PE. The angle of the ultrasonic probe UP is decided so as to approximately coincide with a human body incident angle of the particle beam (i.e., the beam path BP). The angle of the ultrasonic probe UP is defined by the angle which a main axis of the ultrasonic probe UP forms with a human body contact surface. The human body incident angle of the particle beam is, for example, defined by the angle which a beam axis of the particle beam forms with the body surface region RS. The positional relationship between the ultrasonic probe UP and the ultrasonic scanning region US is set in advance in accordance with the ultrasonic probe used for radiotherapy and its ultrasonic scanning region. Note that the ultrasonic scanning region US may be a two-dimensional space (a scanning surface), or may be a three-dimensional space defined by a plurality of scanning surfaces arranged in a row. Whether the ultrasonic scanning region US is a two-dimensional space or a three-dimensional space can be selected at the discretion of the user.

As described above, deciding the placement position of the ultrasonic probe UP in the vicinity of the incident point PE makes it possible to estimate the range with high accuracy based on the ultrasonic image acquired via the ultrasonic probe UP positioned at the placement. It is assumed that the cross section of the radiotherapy plan CT image and the scanning surface of the ultrasonic scanning region US are approximately the same plane in FIG. 5, but this embodiment is not limited thereto. As long as the ultrasonic scanning region US includes the tumor region RC, the cross section of the radiotherapy plan CT image and the scanning surface of the ultrasonic scanning region US may be in any positional relationship.

Upon executing step SC, the particle beam radiotherapy apparatus 1 performs particle beam radiotherapy (step SC). In step SC, the main control circuitry 63 of the particle beam radiotherapy apparatus 1 executes the operation program according to this embodiment. By the execution of the operation program according to this embodiment, the main control circuitry 63 performs immediate estimation of the sighting point of the Bragg peak by using the ultrasonic image and control of the particle beam by using the sighting point.

Hereinafter, a description will be given to the procedure of the particle beam radiotherapy system 100 in step SC in FIG. 3. FIG. 6 shows the procedure of the particle beam radiotherapy system 100 in step SC in FIG. 3.

As shown in FIG. 6, the ultrasonic diagnostic apparatus 3, first of all, acquires an ultrasonic image by using the ultrasonic probe placed at the probe placement position decided in step SB, prior to particle beam irradiation by the particle beam radiotherapy apparatus 1 (step SC1).

FIG. 7 shows an overview surrounding the subject P in the particle beam radiotherapy. As shown in FIG. 7, the particle beam is applied towards the subject P from the radiation head 35 (not shown) in the particle beam radiotherapy. A medical practitioner such as a technologist positions the ultrasonic probe UP at the placement position decided in step SB. In a case where the arm 52 is to be automatically positioned, the arm 52 will be automatically positioned at the placement position decided in step SB. The placement decided in step SB is, for example, preferably displayed by a drawing on the display installed in a radiotherapy room. A medical practitioner such as a technologist refers to the drawing displayed on the display 57, and positions the ultrasonic probe UP so that the ultrasonic probe UP does not enter into the irradiation region of the particle beam indicated on the subject P by the projector. In addition, the placement decided in step SB may be indicated by numerical values as coordinates of the ultrasonic probe UP in the display 57. In this case, the medical practitioner positions the ultrasonic probe UP so that the coordinates detected by a position sensor and an angle sensor provided in the ultrasonic probe UP coincide with the coordinates of the placement decided in step SB.

Furthermore, the processing circuitry 51 determines whether the placement of the ultrasonic probe UP is appropriate or not by the placement decision function 518 as described above. Namely, the processing circuitry 51 performs a determination on whether or not the placement of the ultrasonic probe UP is within a permissible shift range with respect to the placement decided in step SB. Specifically, the processing circuitry 51 can evaluate a shift between the coordinates detected by the position sensor or the angle sensor of the ultrasonic probe UP and the coordinates of the placement decided in step SB, and perform the determination based on the coordinates of the ultrasonic probe UP detected by a camera installed in the radiotherapy room.

The console 50 of the ultrasonic diagnostic apparatus 3 scans inside the body of the subject P with ultrasonic waves via the ultrasonic probe UP. Since the ultrasonic probe UP is placed at the placement position decided in step SB, the radiotherapy target tumor is included in the ultrasonic scanning region. The console 50 of the ultrasonic diagnostic apparatus 3 repeatedly generates the ultrasonic image based on an echo signal from the ultrasonic probe UP. The generated ultrasonic image is, for example, immediately supplied to the particle beam radiotherapy apparatus 1 in a 1 frame unit. In the particle beam radiotherapy, the subject P is breathing, and their chest and abdomen move with breathing. Since the actual range of the particle beam is a distance from the incident point of the subject body surface, it is difficult to match the sight of the Bragg peak with the intended planned point of the Bragg peak in all time phases. Accordingly, the particle beam radiotherapy apparatus 1 according to this embodiment estimates a position on which the sight of the Bragg peak is actually set by using the ultrasonic images.

The following steps SC2 to SC11 are performed in an ultrasonic image 1 frame unit. Processing of steps SC2 to SC11 does not need to be performed for all the frames acquired by the ultrasonic diagnostic apparatus 3, and the processing may be performed for every predetermined frame, such as for every 5 frames.

Upon executing step SC1, the main control circuitry 63 of the particle beam radiotherapy apparatus causes the processing circuitry 51 to execute the registration function 512 (step SC2). In step SC2, the processing circuitry 51 registers the radiotherapy plan CT image with the ultrasonic image.

Figure 8:
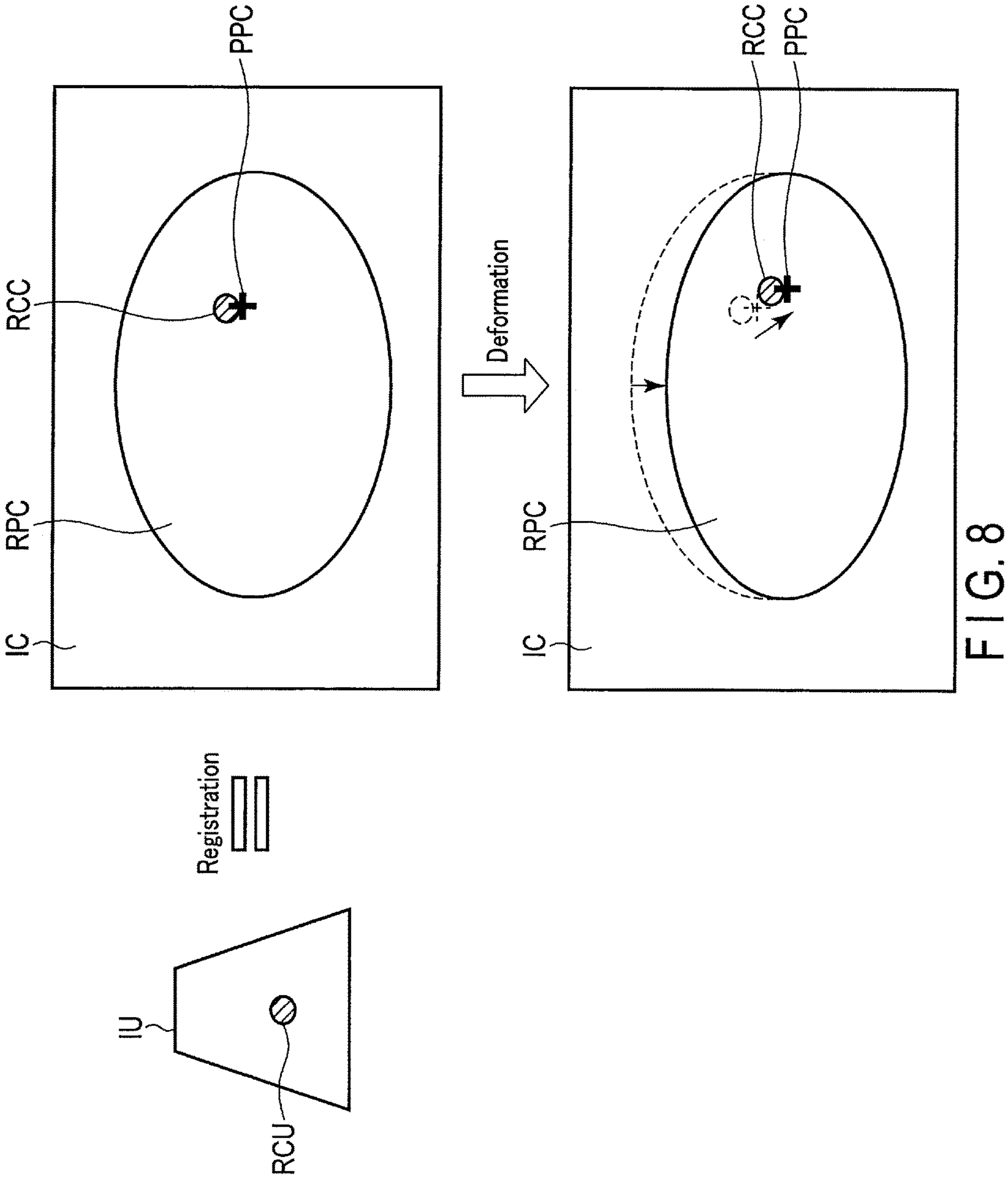
FIG. 8 is a view for explaining processing in step SC2 in FIG. 6.

FIG. 8 is a view for explaining processing in step SC2. As shown in FIG. 8, the processing circuitry 51 registers the radiotherapy plan CT image IC with the ultrasonic image IU in step SC2. The ultrasonic image IU is immediately acquired in the particle beam radiotherapy, and the radiotherapy plan CT image IC has been acquired in the radiotherapy planning (or a stage earlier than the radiotherapy planning) at the stage earlier than the particle beam radiotherapy. Namely, the ultrasonic image IU accurately delineates current inside the body of the subject P, in comparison to the radiotherapy plan CT image IC. By the registration, the coordinate system of the ultrasonic image IU and the coordinate system of the radiotherapy plan CT image IC coincide with each other. As a registration method, any method may be used, such as rigid body registration by linear conversion and non-rigid body registration (deformable registration) by nonlinear conversion. However, the non-rigid body registration is preferable for estimating a range with high accuracy, as is explained below.

In the case of the non-rigid body registration, the subject region RPC, the tumor region RCC, etc. included in the radiotherapy plan CT image IC are deformed in conformity with the ultrasonic image IU. Since the planned point PPC is set in a partial region included in the tumor region RCC, the position of the planned point PPC will also move in conformity with the deformation of the tumor region RCC, etc. In more detail, the position of the planned point PPC after moving currently indicates an anatomical point on which the sight of the Bragg peak should be set when acquiring the ultrasonic image IU.

Upon executing step SC2, the main control circuitry 63 causes the processing circuitry 51 to execute the Bragg peak planned point specifying function (step SC3). In step SC3, the processing circuitry 51 specifies the planned point of the Bragg peak in the ultrasonic image. Specifically, the processing circuitry 51 first specifies coordinates of the planned point set in the radiotherapy plan CT image. The specified coordinates are three-dimensional coordinates in the coordinate system of the radiotherapy plan CT image. Next, in the ultrasonic image, the processing circuitry 51 plots a point on coordinates which are the same as those of the planned point in the coordinate system of the radiotherapy plan CT image. The plotted point will correspond to the planned point in the ultrasonic image.

Upon executing step SC3, the main control circuitry 63 causes the processing circuitry 51 to execute the region identifying function (step SC4). In step SC4, the processing circuitry 51 identifies the body surface region included in the ultrasonic image. For example, the processing circuitry 51 may identify the body surface region by threshold value processing concerned with luminance values of pixels of the ultrasonic image, or may identify the body surface region by using a precondition that the body surface region is present at an upper end of the ultrasonic image. Alternately, the processing circuitry 51 may identify the body surface region by using other image processing, such as luminance value connection processing. As described above, the ultrasonic probe is placed in the vicinity of the body surface incident point. Accordingly, the body surface region included in the ultrasonic image is located in the vicinity of the body surface incident point. Note that in the case where the body surface incident point is delineated in the ultrasonic image as will be described below, the body surface region will include the body surface incident point. In step SC4, the processing circuitry 51 may identify other image regions, such as the tumor region, included in the ultrasonic image as necessary.

Upon executing step SC4, the main control circuitry 63 causes the processing circuitry 51 to execute the Bragg peak sighting point estimation function (step SC5). In step SC5, the processing circuitry 51 estimates the sighting point of the Bragg peak in the ultrasonic image. Specifically, the processing circuitry 51 plots a position only at the distance corresponding to the planned range from the body surface region RSU in the ultrasonic image as a sighting point PBU. In other words, the straight-line distance between the sighting point PBU and the body surface region is approximately equal to the planned range. It is estimated that the Bragg peak of the particle beam is actually sighted on this sighting point PBU.

Upon executing step SC5, the main control circuitry 63 causes the display 57 to perform display (step SC6). In step SC6, the display 57 displays the ultrasonic image indicating the planned point and the sighting point of the Bragg peak.

FIG. 9 shows an example of the ultrasonic image IU clearly indicating the planned point PPU and the sighting point PBU of the Bragg peak. As shown in FIG. 9, the body surface region RSU and the tumor region RCU are included in the ultrasonic image IU. The Bragg peak planned point PPU is superimposed on the tumor region RCU. As shown in FIG. 9, it can be assumed that the sighting point PBU may shift from the planned point PPU due to the respiratory motion, etc. of the subject P. As shown in FIG. 9, the display 57 displays the ultrasonic image IU clearly indicating the planned point PPU and the sighting point PBU of the Bragg peak. The ultrasonic image IU being displayed allows the medical practitioner to carry out the particle beam radiotherapy while clearly ascertaining the positional relationship between the planned point PPU and the sighting point PBU. As an indication form of the planned point PPU and the sighting point PBU, the display 57 preferably displays the planned point PPU and the sighting point PBU by, for example, marks having mutually different shapes, sizes, colors, etc.

The display form of the planned point and the sighting point of the Bragg peak is not limited to the above method only. The display 57 may display the planned point and the sighting point of the Bragg peak by other display forms as described below.

FIG. 10 shows a superimposed image of the ultrasonic image IU clearly indicating the planned point PPU and sighting point PBU of the Bragg peak and the radiotherapy plan CT image IC. As shown in FIG. 10, the ultrasonic image IU is superimposed onto the radiotherapy plan image IC. Since the radiotherapy plan image IC is registered with the ultrasonic image IU, the ultrasonic image IU and the radiotherapy plan CT image IC are superimposed with high accuracy. In the ultrasonic image IU, the planned point PPU and the sighting point PBU of the Bragg peak are clearly indicated. According to this display form, the medical practitioner can ascertain the positions of the planned point PPU and the sighting point PBU of the Bragg peak in the radiotherapy plan CT image.

Upon executing step SC6, the main control circuitry 63 causes the processing circuitry 51 to execute the range measurement function (step SC7). In step SC7, the processing circuitry 51 measures a distance (an ideal range) from the body surface region to the planned point.

Upon executing step SC7, the main control circuitry 63 causes the irradiation system control circuitry 19 to perform the determination function (step SC8). In step SC8, the irradiation system control circuitry 19 determines whether the difference between the planned range and the actual range is within a permissible amount or not.

Hereinafter, steps SC7 and SC8 will be explained with reference to FIG. 11. FIG. 11 is a view showing the ideal range DSP and the actual range DSB in the ultrasonic image IU. As shown in FIG. 11, the processing circuitry 51 measures a distance from the body surface region RSU to the planned point PPU as the ideal range DSP, and measures a distance from the body surface region RSU to the sighting point PBU as the actual range DSB. In further detail, the ideal range DSP is defined by the distance from a reference point in the body surface region RSU to the planned point PPU. As shown in FIG. 11, the reference point is set at a pixel on the body surface side, not on the internal side of the body surface region RSU. As shown in FIG. 11 for example, among the pixels on the body surface side of the body surface region RSU, the reference point is set at a pixel in the shortest distance from the planned point PPU. Alternately, the reference point may be set at a body surface incident point if the body surface incident point is included in the ultrasonic image IU, and may be set in the vicinity of the body surface incident point if the body surface incident point is not included in the ultrasonic image IU.

Upon measuring the ideal range DSP and the actual range DSB, the irradiation system control circuitry 19 calculates a difference between the ideal range DSP and the actual range DSB, and determines whether the calculated difference is within a preset permissible amount or not. With an increase in the difference, it means that the Bragg peak of the particle beam actually applied from the radiation head 35 is sighted on a position separated from the planned point PPU. In this case, there is a concern that a radiation dose as planned cannot be applied to a tumor, and also that normal tissues may be damaged. The permissible amount can be set to a given value by a medical practitioner, etc.

The ideal range DSP and the actual range DSB are not limited to being measured in an ultrasonic image. Namely, the ideal range DSP and the actual range DSB may be measured in the radiotherapy plan CT image after the registration.

FIG. 12 shows the ideal range DSP and the actual range DSB in the radiotherapy plan CT image IC. As shown in FIG. 12, the radiotherapy plan CT image IC includes a body surface incident point PE. Thus, the ideal range DSP and the actual range DSB can be measured more precisely in comparison to the case of measuring in the ultrasonic image. Namely, the ideal range DSP is measured as a distance from the body surface incident point PE to the planned point PPC, and the actual range DSB is measured as a distance from the body surface incident point PE to the sighting point PBC.

In a case of determining that the difference is within the permissible amount in step SC8 (step SC8: YES), the irradiation system control circuitry 19 starts irradiation of a particle beam at an opportunity of a radiotherapy start instruction from the user via the input interface 59, etc. (step SC9). In step SC9, the irradiation system control circuitry 19 applies a radiotherapy target tumor in the body of the subject P with a particle beam by controlling the radiation head 35 in accordance with the radiotherapy plan information decided in step SA. For example, a particle beam having energy in conformity with the range set in the radiotherapy planning is applied.

Upon executing step SC9, the main control circuitry 63 determines whether or not all the planned irradiations have been completed (step SC10). If it is determined that all the irradiations have not been completed in step SC10 (step SC10: No), the main control circuitry 63 returns again to step SC2, and under the particle beam irradiation, performs processing from step SC2 to step SC10 based on the next ultrasonic image.

On the other hand, if it is determined that the difference is not within the permissible amount in step SC8 (step SC8: No), the irradiation system control circuitry 19 stops the particle beam irradiation by controlling the radiation head 35

(step SC10). By stopping the particle beam irradiation, it is possible to prevent normal tissues from being damaged. Note that if it is determined that the difference is not within the permissible amount at the stage where the particle beam has not been applied in step SC8 (step SC8: No), the stoppage of the particle beam irradiation will be continued.

Until it is determined that all the irradiations have been ended in step SC10 or until the particle beam irradiation is stopped in step SC11, the main control circuitry 63 performs processing from step SC2 to step SC11 based on the latest ultrasonic image.

Then, if it is determined that all the irradiations have been ended in step SC10 (step SC10: Yes) or the particle beam irradiation is stopped in step SC11, the main control circuitry 63 ends the particle beam radiotherapy.

By the above, the description of the procedure of the particle beam radiotherapy system 100 in the particle beam radiotherapy ends.

The above procedure of the particle beam radiotherapy system 100 in the particle beam radiotherapy as shown in FIG. 6 is an example, and various modifications are possible. For example, steps SC7, SC8, and SC9 may be omitted. In this case, the medical practitioner may determine whether or not to continue the particle beam irradiation by observing the positional relationship between the sighting point and the planned point displayed in the display 57 in step SC6.

In addition, step SC6 of the above procedure of the particle beam radiotherapy system 100 in the particle beam radiotherapy as shown in FIG. 6 may be omitted. In this case, switching between irradiation and a stoppage of the irradiation of the particle beam will be performed by the irradiation system control circuitry 19, without performing the display of the ultrasonic image clearly indicating the planned point and the sighting point of the Bragg peak.

Although single-field irradiation is assumed in the above embodiment, this embodiment is not limited to the single-field irradiation and is applicable to multi-field irradiation. In this case, steps SC2 to SC11 can be repeated for each of irradiation directions of particle beams.

In the above embodiment, the body surface region of the subject P is to be identified from the radiotherapy plan CT image or the ultrasonic image in the particle beam radiotherapy. However, the present embodiment is not limited thereto. For example, a body surface region may be identified from a cone-beam CT image acquired by photographing the subject P by an X-ray computed tomography apparatus installed in the radiotherapy room where the particle beam radiotherapy apparatus 1 is installed, immediately before the particle beam radiotherapy. Thereby, the processing circuitry 51 can identify the body surface region by using the CT image immediately before the particle beam radiotherapy, which is closer to the shape of the subject in the particle beam radiotherapy than the radiotherapy plan image in the radiotherapy planning. It is thus possible to estimate the sighting point, etc. of the Bragg peak with high accuracy.

As an image for identifying the body surface region, an ultrasonic image acquired by the ultrasonic diagnostic apparatus immediately before the particle beam radiotherapy may be used. In this case, it is preferable that the ultrasonic image is acquired by placing an ultrasonic probe at a body surface incident point. Thereby, the body surface incident point is delineated in the acquired ultrasonic image. In addition, it is preferable that the ultrasonic probe is placed so that the angle of the ultrasonic probe coincides with the angle of the beam path of the particle beam. This placement of the ultrasonic probe makes it possible to measure the ideal range with higher accuracy based on the ultrasonic image.

Furthermore, in the above descriptions, the placement position of the ultrasonic probe is to be decided so that the ultrasonic scanning region US can include the tumor region RC, and the ultrasonic probe UP is positioned in the vicinity of the incident point of the particle beam into the body surface of the subject P (the first placement deciding method). However, the present embodiment is not limited thereto. For example, the following second placement deciding method and third placement deciding method can be considered.

FIG. 13 shows the placement of the ultrasonic probe decided by the second placement deciding method. As shown in FIG. 13, in the second placement deciding method, the processing circuitry 51 decides the placement of the ultrasonic probe UP so that the ultrasonic scanning region US can include the tumor region RC and the incident point PE. In more detail, the position PUP of the ultrasonic probe UP is decided at a position where the ultrasonic scanning region US can include both of the tumor region RC and the incident point PE, and is separated from the incident point PE. There is no particular limitation to the angle of the ultrasonic probe UP. The actual range of the particle beam is measured, for example, as follows. The processing circuitry 51 identifies the body surface incident point PE included in the ultrasonic image, and measures a distance from the tumor region RCU to the body surface incident point PEO as an actual range.

If the ultrasonic probe is positioned at the placement decided by the second placement deciding method, the tumor region and the body surface incident point are included in the ultrasonic image. In this case, the processing circuitry 51 can specify the body surface incident point in the ultrasonic image. For example, the processing circuitry 51 specifies three-dimensional coordinates of the body surface incident point delineated in the radiotherapy plan CT image, and plots a point on a pixel on the same coordinates as the specified three-dimensional coordinates among pixels of the ultrasonic image. The plotted point corresponds to the body surface incident point. The processing circuitry 51 can measure a distance from the body surface incident point to the planned point in the ultrasonic image as an ideal range. A planned point of the Bragg peak in the ultrasonic image may be specified by a method similar to that in step SC4 in FIG. 6. According to the second placement deciding method, in comparison to the above first placement deciding method, it is possible to measure a range more precisely since the body surface incident point is included in the ultrasonic image.

FIG. 14 shows the placement of the ultrasonic probe decided by the third placement deciding method. As shown in FIG. 14, in the third placement deciding method, the processing circuitry 51 decides the placement of the ultrasonic probe UP so that the ultrasonic scanning region US can include the tumor region RC and the incident point PEO of the particle beam into an organ including the tumor. As for the third placement deciding method, its application is assumed in a case where there is air between an incident point of the subject P and an organ including a tumor. Specifically, a case of irradiating a tumor in the liver with a particle beam across the lungs can be assumed.

As shown in FIG. 14, the radiotherapy plan CT image according to the third method includes an image region (to be referred to as a liver region hereinafter) RLI concerning the liver including the tumor and image regions (to be referred to as a lung region hereinafter) RLU concerning the lungs. The lung regions RLU are positioned closer to the body surface region RS side than the liver region RLI. A beam path BP of the particle beam is set to pass through the tumor region RCU. A crossing point of the beam path BP of the particle beam and a surface of the liver region RLI is defined as a body surface incident point PEO into the liver region RLI. The position PUP of the ultrasonic probe UP is decided at a position where the ultrasonic scanning region US can include both of the tumor region RC and the incident point PEO. There is no particular limitation to the angle of the ultrasonic probe UP.

If the ultrasonic probe is positioned at the placement decided by the third placement deciding method, an organ incident point is included in the ultrasonic image. First, the processing circuitry 51 specifies a planned point of the Bragg peak and an organ incident point in the ultrasonic image by a method similar to the method in step SC4 in FIG. 6. Then, the processing circuitry 51 specifies the organ incident point into the liver region included in the ultrasonic image, and measures the first distance from the organ incident point to the planned point. Next, the processing circuitry 51 measures the second distance from the body surface incident point to the organ incident point in the radiotherapy plan CT image. Next, the processing circuitry 51 calculates a path length (to be referred to as a lung path length) of the lung region along the beam path in the radiotherapy plan CT image. Then, the processing circuitry 51 calculates a distance of a sum of the first and second distances from which the lung path length is subtracted, as an ideal range. According to the third placement deciding method, even if air is present between the body surface incident point and the planned point along the beam path, it is possible to measure the range more precisely.

In a case of using the third placement deciding method, it is possible to specify a sighting point without using body surface information. Namely, since a change in thickness of the peripheral regions of the lungs due to respiration is small, and the distance of the second distance from which the lung path length is subtracted can be considered constant, it is possible to specify the sighting point based on the position of the organ incident point in the ultrasonic image. The organ incident point in the ultrasonic image may be obtained based on the radiotherapy plan CT image IC, or may be obtained by specifying coordinate conversion between the ultrasonic image IU and the real space by a position sensor to be described below to plot the beam path BP on the ultrasonic image IU.

Which one of the first placement deciding method, the second placement deciding method, and the third placement deciding method is used may be set in advance, or may be selected at the discretion of a medical practitioner, etc. via the input interface 59. For example, the first placement deciding method and the second placement deciding method are suitable for the case where soft tissues are consecutive in a beam path. The third placement deciding method is suitable for the case where air is present in a beam path.

In the above embodiment, the processing circuitry 51 may execute the coordinate detection function 517 to estimate a sighting point of the Bragg peak, an actual range, an ideal range, etc. with higher accuracy by using an output signal from the position sensor. The position sensor is, for example, a position sensor or an angle sensor (to be referred to as a probe sensor hereinafter) mounted on the ultrasonic probe. As a probe sensor, for example, an existing magnetic type or electric type sensor is available. In addition, by providing a joint portion or an extension portion of the arm 52 with a sensor such as a potentiometer, this can be made to function as a probe sensor. Hereinafter, a real-space coordinate system defined by the probe sensor will be referred to as a real-space probe coordinate system.

The processing circuitry 51 specifies three-dimensional coordinates in the real-space probe coordinate system of the ultrasonic probe based on the output signal from the probe sensor. The real-space probe coordinate system of the ultrasonic probe and the image coordinate system (to be referred to as an ultrasonic image coordinate system hereinafter) of the ultrasonic image are associated in advance. The processing circuitry 51 specifies three-dimensional coordinates of the planned point in the real-space probe coordinate system based on the three-dimensional coordinates of the ultrasonic probe in the real-space probe coordinate system, and the coordinates of the ultrasonic image coordinate system of the planned point included in the ultrasonic image. Similarly, based on the three-dimensional coordinates of the ultrasonic probe in the real-space probe coordinate system and coordinates of a body surface incident point, or its near point included in the ultrasonic image in the ultrasonic image coordinate system, the processing circuitry 51 specifies three-dimensional coordinates of the body surface incident point or its near point in the real-space probe coordinate system. The processing circuitry 51 can estimate an ideal range in the real-space probe coordinate system based on three-dimensional coordinates of the body surface incident point or its near point and the three-dimensional coordinates of the planned point in the real-space coordinate system.

The specifying of three-dimensional coordinates of a body surface incident point in a real-space coordinate system, such as a real-space probe coordinate system, is not limited only to the method of using a probe sensor. For example, a three-dimensional sensor may be used instead of a probe sensor. As a three-dimensional sensor, a distance image sensor or an ultrasonic sensor may be used. By the three-dimensional sensor, three-dimensional coordinates of a body surface incident point in the particle beam radiotherapy are detected. Thus, the three-dimensional sensor is installed so that a sensing range of the three-dimensional sensor includes the body surface incident point of the subject P. Hereinafter, the real-space coordinate system defined by the three-dimensional sensor is to be referred to as a real-space 3D coordinate system. By this configuration, the processing circuitry 51 specifies a body surface incident point of the subject P in the real-space 3D coordinate system based on an output signal from the three-dimensional sensor. Thereby, even in a case where the body surface incident point is not included in the ultrasonic image, it is possible to specify three-dimensional coordinates of the body surface incident point in the real-space coordinate system.

The specifying of three-dimensional coordinates of a body surface incident point is not limited only to a method of using a probe sensor or a 3D sensor. For example, the processing circuitry 51 may specify three-dimensional coordinates of a body surface incident point by Epipolar geometric theory. Specifically, to start, images obtained by photographing a body surface incident point from two or more directions by an optical camera, an X-ray diagnostic apparatus, etc. are acquired. Next, the processing circuitry 51 specifies the body surface incident point included in an image of each direction in accordance with an instruction by image processing or by a medical practitioner, etc. via the input interface 59. Then, the processing circuitry 51 can calculate three-dimensional coordinates of the body surface incident point in a real-space coordinate system by applying epipolar geometry to the body surface incident point included in an image of each direction.

Furthermore, the three-dimensional coordinates of the body surface incident point may be specified by other methods. For example, a belt is wound around the subject P in order to suppress the respiratory motion of the subject P during the particle beam radiotherapy. A magnetic-type or electric-type position sensor may be mounted on the surface of this belt. Based on an output signal of the position sensor, the processing circuitry 51 can specify the three-dimensional coordinates of the body surface incident point in the real-space coordinate system.

In addition, in the above step SC8 in FIG. 6, the irradiation system control circuitry 19 is to switch between irradiation and a stoppage of the irradiation of the particle beam according to a difference between an ideal range and an actual range. However, the present embodiment is not limited thereto. For example, the irradiation system control circuitry 19 switches between irradiation and a stoppage of the irradiation based on a position of a tumor region or a planned point and an actual range. In more detail, the irradiation system control circuitry 19 continues particle beam irradiation if a tumor region or a planned point is present in a traveling direction of a particle beam, and the tumor region or the planned point is at a position of an actual range of the particle beam and in its vicinity. On the other hand, the irradiation system control circuitry 19 stops the particle beam if the tumor region or the planned point is not present in the traveling direction of the particle beam, or the tumor region or the planned point is not at the position of the actual range of the particle beam and in its vicinity.

Whether or not the tumor region or the planned point is present in the traveling direction of the particle beam is determined based on, for example, whether or not the tumor region or the planned point is present on a beam path or on an extended line of the beam path in the ultrasonic image or the radiotherapy plan CT image. Whether or not the tumor region or the planned point is at the position of the actual range of the particle beam and in its vicinity is determined, for example, by measuring a difference between a position of a distance corresponding to the actual range away from the body surface region and a position of the tumor region or the planned point, and based on whether or not the difference is larger than a threshold value. If the difference is larger than the threshold value, it is determined that the tumor region or the planned point is not at the position of the actual range of the particle beam and in its vicinity, and if the difference is smaller than the threshold value, it is determined that the tumor region or the planned point is at the position of the actual range of the particle beam and in its vicinity. By this switching method, in comparison to the case of considering only a difference between the actual range and the ideal range, irradiation and a stoppage of the irradiation of the particle beam can be switched in consideration of the positional relationship between the beam path of the particle beam and the tumor region or the planned point.

In the above procedure as shown in FIG. 6, if the difference between the ideal range and the actual range is not within a permissible amount, the irradiation of the particle beam is to be stopped. However, the present embodiment is not limited thereto. Namely, if the difference is not within the permissible amount, the actual range may be adjusted so that the difference will be reduced. This embodiment will be described below.

Figure 15:
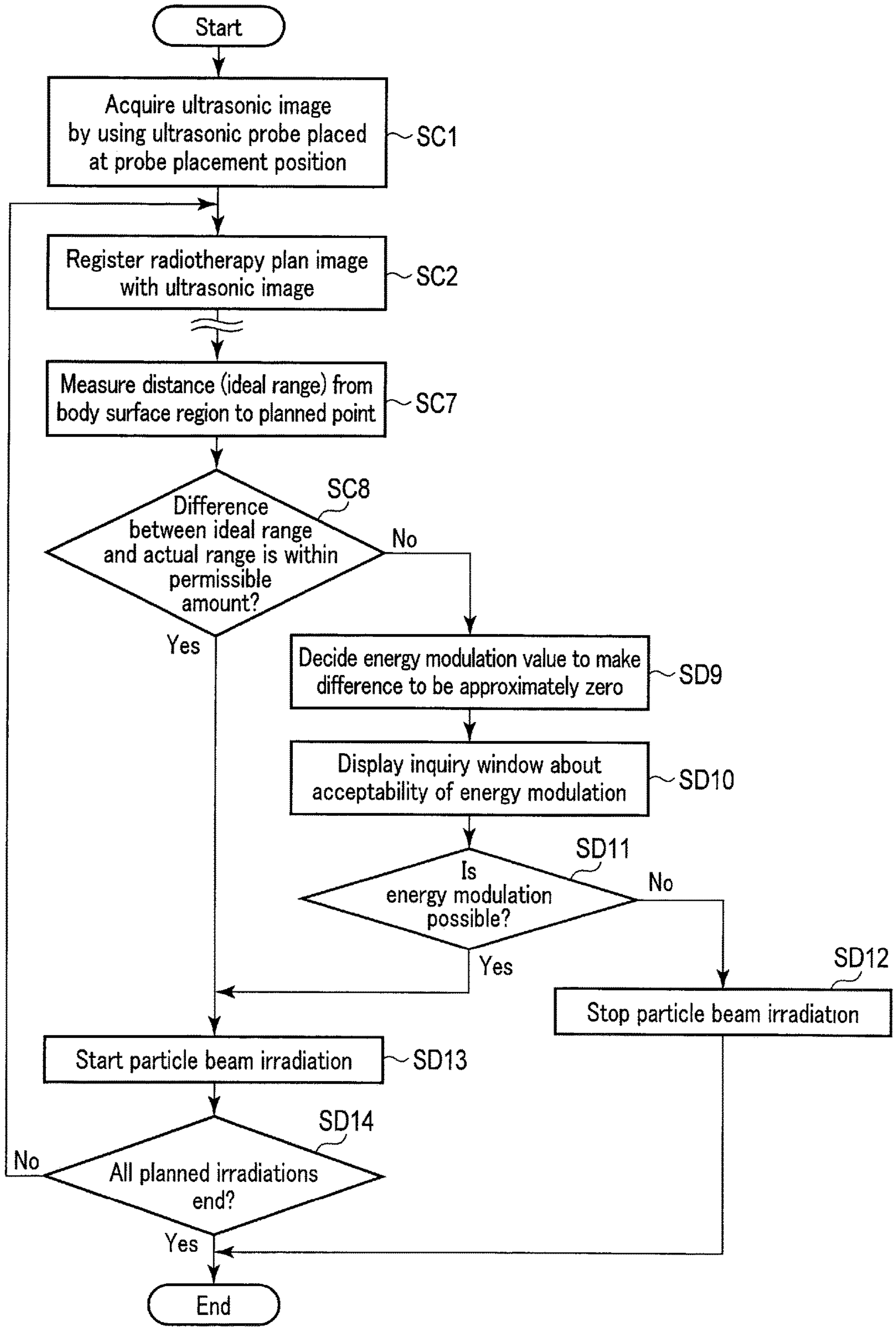
FIG. 15 is a flowchart showing another procedure of the particle beam radiotherapy system in step SC in FIG. 3.

FIG. 15 shows another procedure of the particle beam radiotherapy system in step SC in FIG. 3. In the description below, the processing that is approximately the same as those in FIG. 6 will be denoted by the same reference symbols, and a repetitive description will be given only where necessary.

As shown in FIG. 15, steps SC1 to SC8 are the same as those in FIG. 6. If it is determined that the difference between the ideal range and the actual range is within the permissible amount in step SC8 (step SC8: Yes), the irradiation system control circuitry 19 starts the irradiation of the particle beam in response to a radiotherapy start instruction from a user via the input interface 59, etc. (step SD13). In step SD13, the irradiation system control circuitry 19 controls the radiation head 35 in accordance with the radiotherapy plan information decided in step SA, and applies a particle beam to the radiotherapy target tumor inside the body of the subject P. For example, a particle beam having energy in conformity with the range set in the radiotherapy planning is applied.

Upon executing step SD13, the main control circuitry 63 determines whether all the planned irradiations have been ended or not (step SD14). If it is determined that all the irradiations have not been ended in step SD14 (step SD14: No), the main control circuitry 63 returns to step SC2 again, and under the particle beam irradiation, performs the processing from step SC2 to step SC14 based on the next ultrasonic image.

However, if it is determined that the difference is not within the permissible amount in step SC8 (step SC8: No), the irradiation system control circuitry 19 decides an energy modulation value for making the difference to be approximately zero (step SD9). The energy modulation value is defined by a difference between a current energy setting value of a particle beam applied from the radiation head 35 and an energy setting value after being changed. The irradiation system control circuitry 19, for example, decides an energy modulation value by using a difference/modulation value table. The difference/modulation value table is stored in, for example, the storage circuitry 61.

FIG. 16 shows an example of the difference/modulation value table used in step SD9 in FIG. 15. The difference/modulation value table associates an energy modulation value with each difference between an ideal range and an actual range. The difference is defined by a subtraction value of an actual range from an ideal range. In the difference/modulation value table, for example, differential values are registered every 1 mm from an upper limit to a lower limit. The energy modulation value is defined by a subtraction value of the setting value after being changed from the current setting value of the energy of the particle beam applied from the radiation head 35, for increasing or decreasing a range for only a corresponding differential value. For example, if an actual range is only −10 mm shorter than an ideal range, the actual range needs to be increased for +10 mm. Assuming that for increasing the actual range for +10 mm, for example, the energy of the particle beam made incident into the subject P needs to be increased for +1 MeV. In this case, as shown in FIG. 16, the energy modulation value corresponding to the differential value "−10 mm" is "+1 MeV." The relationship between the differential value and the energy modulation value is preferably determined by an experiment, etc. in advance. The differential value and the energy modulation value can be discretionarily changed by a medical practitioner, etc. via the input interface 59.

The irradiation system control circuitry 19 decides, based on the difference calculated in step SC8, an energy modulation value associated with the difference by using the difference/modulation value table. Specifically, upon inputting the difference calculated in step SC8 into the difference/modulation value table, an energy modulation value associated with the difference will be output. The energy modulation value deciding method is not limited only to the method of using the difference/modulation value table. For example, an energy modulation value may be calculated from a differential value in accordance with a relational expression between a differential value and an energy modulation value.

When step SD9 is executed, the main control circuitry 63 displays an inquiry screen of the propriety of energy modulation in the display 57 (step SD10).

FIG. 17 shows an example of an inquiry screen IS displayed in step SD10 in FIG. 15. The inquiry screen IS has a display column IS1, an accept button IS2, and a reject button IS3. The display column IS1 displays a message concerning an inquiry of whether to permit the energy modulation or not. For example, as shown in FIG. 17, "Change particle beam energy to adjust sighting point to planned point of Bragg peak?" is displayed. The accept button IS2 is a display button for notifying the particle beam radiotherapy apparatus 1 of acceptance of the energy modulation. If the accept button IS2 is pressed down, a permission signal of the energy modulation is supplied to the main control circuitry 63. The reject button IS3 is a display button for notifying the particle beam radiotherapy apparatus 1 of rejection of the energy modulation. If the reject button IS3 is pressed down, a rejection signal of the energy modulation is supplied to the main control circuitry 63.

Upon displaying the inquiry screen IS, the main control circuitry 63 waits for a response from the medical practitioner via the input interface 59 (step SD11). If the energy modulation is rejected (step SD11: NO), the main control circuitry 63 supplies the rejection signal to the irradiation system control circuitry 19. The irradiation system control circuitry 19 controls the radiation head 35 to stop the particle beam irradiation.

On the other hand, if the energy modulation is permitted (step SD11: YES), the main control circuitry 63 supplies the permission signal and the energy modulation value to the irradiation system control circuitry 19. The irradiation system control circuitry 19 controls the radiation head 35 in accordance with the energy modulation value to reduce the difference between the actual range and the planned range to be approximately zero. The modulation of energy is performed by, for example, changing the thickness concerning the particle beam irradiation directions of various kinds of particle beam filters, such as a ridge filter, a bolus filter, a multileaf collimator, and a range shifter, which are provided in the rotating portion 33. For example, a particle beam filter having different thickness in accordance with the lateral-direction position is incorporated in the radiation head 35 so as to be slidable in the lateral direction by an actuator, etc. In a case where the particle beam energy is increased, the irradiation system control circuitry 19 drives an actuator to slide the particle beam filter in the lateral direction, and increases the thickness of the particle beam filter on the beam path. In a case where the particle beam energy is reduced, the irradiation system control circuitry 19 drives the actuator to slide the particle beam filter in the lateral direction, and reduces the thickness of the particle beam filter on the beam path.

The modulation of energy may be performed by changing energy of a particle beam given by an accelerator 11. In this case, the main control circuitry 63 supplies a permission signal and an energy modulation value to an acceleration system control circuitry 13. The acceleration system control circuitry 13 calculates an additional value of the energy setting value and the energy modulation value, and accelerates the particle beam so that the particle beam having energy corresponding to the additional value will be applied from the radiation head 35. This makes it possible to reduce the difference between the ideal range and the actual range to be approximately zero.

Until it is determined that all the irradiations have been ended in step SD14 or if the irradiation of the particle beam is stopped in step SD12, the main control circuitry 63 repeats steps SC2 to SD14 based on the latest ultrasonic image. Then, if it is determined that all the irradiations have been ended in step SD14 (step SD14: YES) or the irradiation of the particle beam is stopped in step SD12, the main control circuitry 63 ends the particle beam radiotherapy.

As such, according to the present embodiment, it is possible to adjust the energy of the particle beam made incident into the subject P so that the difference between the ideal range and the actual range will be approximately zero. This allows the actual range to follow the ideal range in approximate real time. As is different from the procedure shown in FIG. 6, in the procedure shown in FIG. 15, the particle beam radiotherapy can be continued without stopping the irradiation of the particle beam, even if the difference is not within the permissible amount. This can improve the throughput of the particle beam radiotherapy.

Note that the procedure shown in FIG. 15 is not limited thereto. For example, in the procedure shown in FIG. 15, when the difference is not within the permissible amount in step SC8, an energy modulation value is decided. However, the present embodiment is not limited thereto. For example, when the difference largely deviates from the permissible amount in step SC8, the energy modulation value is not decided, and the irradiation of the particle beam may be stopped. For example, if the difference calculated in step SC8 is larger than the maximum value of the differential value registered in the difference/modulation value table, the irradiation of the particle beam may be stopped.

In addition, in the above embodiment, the probe placement decision function 511, the registration function 512, the region identifying function 513, the Bragg peak planned point specifying function 514, the Bragg peak sighting point estimation function 515, the range measurement function 516, and the coordinate detection function 517 are to be executed by the processing circuitry 51 of the particle beam radiotherapy apparatus 1. However, the present embodiment is not limited thereto. For example, at least one of the probe placement decision function 511, the registration function 512, the region identifying function 513, the Bragg peak planned point specifying function 514, the Bragg peak sighting point estimation function 515, the range measurement function 516, and the coordinate detection function 517 may be mounted on the ultrasonic diagnostic apparatus 3 or the radiotherapy planning apparatus 5.

In addition, in the above embodiment, the processing of FIG. 6 or FIG. 15 is performed by using the ultrasonic image acquired in the particle beam radiotherapy. However, the present embodiment is not limited thereto. For example, in a case where a time series of ultrasonic images of the same region of the same patient to be treated are acquired before radiotherapy, steps SC2 to SC10 in FIG. 6 or steps SC2 to SD14 in FIG. 15 may be performed based on the ultrasonic images.

As has been described above, the particle beam radiotherapy system 100 according to the present embodiment includes the gantry 17, the ultrasonic diagnostic apparatus 3, the processing circuitry 51, and the display 57. The gantry

17 applies particle beams to the subject P. The ultrasonic diagnostic apparatus 3 scans the subject P with ultrasonic waves via the ultrasonic probe, and acquires an ultrasonic image concerning a tumor of the subject P. The processing circuitry 51 specifies the second planned point of the Bragg peak in the ultrasonic image, which anatomically coincides approximately with the first planned point of the Bragg peak decided in the radiotherapy planning. The processing circuitry 51 estimates a sighting point of the Bragg peak of a particle beam applied by the gantry 17 based on a body surface region included in the ultrasonic image and an actual range of the particle beam applied by the gantry 17. The display circuitry 57 displays the ultrasonic image to indicate the second planned point and the sighting point.

The above arrangement allows the processing circuitry 51 according to the present embodiment to estimate the sighting point which is a position on which the Bragg peak of the particle beam applied from the gantry 17 is sighted in the particle beam radiotherapy based on the ultrasonic image acquired by a relatively inexpensive and compact ultrasonic diagnostic apparatus. By displaying the ultrasonic image to indicate the estimated sighting point and the planned point, the display 57 can allow a medical practitioner, etc. to clearly ascertain the positional relationship between the sighting point and the planned point.

According to this embodiment, it is therefore possible to easily confirm a position of the Bragg peak.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A particle beam radiotherapy system comprising:

a gantry configured to apply particle beams to a subject;

an ultrasonic diagnostic apparatus configured to scan the subject with ultrasonic waves via an ultrasonic probe, and acquire an ultrasonic image concerning a radiotherapy target region of the subject;

processing circuitry configured to specify a first planned point of a Bragg peak in the ultrasonic image, which anatomically coincides approximately with a second planned point of the Bragg peak determined using a radiotherapy planning apparatus, the first planned point and the second planned point being positioned so as to be included in the radiotherapy target region, and estimate a sighting point of the Bragg peak of a particle beam applied by the gantry based on information concerning a body surface position of the subject and an actual range of the particle beam applied by the gantry; and a display configured to display the ultrasonic image so as to indicate the first planned point and the sighting point.

2. The particle beam radiotherapy system of claim 1, wherein the information concerning the body surface position is a body surface region concerning the subject in the ultrasonic image.

3. The particle beam radiotherapy system of claim 2, wherein the processing circuitry decides placement of the ultrasonic probe for acquiring the ultrasonic image in particle beam radiotherapy, based on an irradiation direction of the particle beam applied from the gantry.

4. The particle beam radiotherapy system of claim 3, wherein the processing circuitry decides a vicinity of an incident point of the particle beam from the gantry into a body surface of the subject as the placement of the ultrasonic probe, based on the irradiation direction.

5. The particle beam radiotherapy system of claim 3, wherein the processing circuitry decides the placement of the ultrasonic probe so that both of the radiotherapy target region and an incident point of the particle beam from the gantry into the body surface of the subject are included in an ultrasonic scanning region.

6. The particle beam radiotherapy system of claim 3, wherein the processing circuitry decides the placement of the ultrasonic probe so that both of the radiotherapy target region and an incident point of the particle beam into an organ including the radiotherapy target region are included in the ultrasonic scanning region.

7. The particle beam radiotherapy system of claim 2, further comprising control circuitry configured to switch between irradiation and a stoppage of the irradiation of the particle beam by the gantry based on a comparison between an actual range of the particle beam applied by the gantry and an ideal range from the body surface region to the first planned point.

8. The particle beam radiotherapy system of claim 7, wherein the processing circuitry registers a medical image targeted for the radiotherapy target region acquired in radiotherapy planning with the ultrasonic image, specifies a third planned point of the Bragg peak in the registered medical image, which anatomically coincides approximately with the second planned point, and decides a distance from a body surface region in the registered medical image to the third planned point as the ideal range.

9. The particle beam radiotherapy system of claim 1, further comprising control circuitry, wherein the processing circuitry identifies a radiotherapy target region included in the ultrasonic image by image processing, and wherein the control circuitry switches between irradiation and a stoppage of the irradiation of the particle beam by the gantry based on the radiotherapy target region or a position of the first planned point and the actual range.

10. The particle beam radiotherapy system of claim 1, further comprising a position sensor mounted on the ultrasonic probe, wherein the processing circuitry detects three-dimensional coordinates of the ultrasonic probe in a real-space coordinate system based on an output signal from the position sensor, specifies coordinates of a radiotherapy target region in an image coordinate system which defines the ultrasonic image, and estimates coordinates of the sighting point in the real-space coordinate system or the image coordinate system based on the actual range by using the coordinates of the ultrasonic probe in the real-space coordinate system and the coordinates of the radiotherapy target region in the image coordinate system.

11. The particle beam radiotherapy system of claim 10, wherein the processing circuitry detects coordinates of an incident point of the particle beam from the gantry into the body surface of the subject in the real-space coordinate system.

12. The particle beam radiotherapy system of claim 11, wherein the detected coordinates are used as information concerning the body surface position.

13. The particle beam radiotherapy system of claim 2, further comprising control circuitry configured to modulate energy of the particle beam applied from the gantry in accordance with a difference between the actual range of the particle beam applied from the gantry and an ideal range from the body surface region to the first planned point so as to reduce the difference.

14. The particle beam radiotherapy system of claim 13, further comprising storage circuitry configured to store in each of a plurality of differential values an association with a modulation value of the energy of the particle beam for reducing the differential value to be approximately zero, wherein if the difference is within a permissible amount, the control circuitry decides a modulation value corresponding to the difference based on the association, and modulates the energy of the particle beam applied from the gantry in accordance with the decided modulation value.

15. The particle beam radiotherapy system of claim 13, further comprising:

a display configured to display an inquiry of whether to modulate the energy of the particle beam; and input circuitry configured to input a response to the inquiry, wherein the control circuitry modulates the energy of the particle beam applied from the gantry if a response of adopting is input via the input circuitry.

16. A particle beam radiotherapy system, comprising:

a gantry configured to apply particle beams to a subject;

an ultrasonic diagnostic apparatus configured to scan the subject with ultrasonic waves via an ultrasonic probe, and acquire an ultrasonic image concerning a radiotherapy target region of the subject;

processing circuitry configured to specify a first planned point of a Bragg peak in the ultrasonic image, which anatomically coincides approximately with a second planned point of the Bragg peak determined using a radiotherapy planning apparatus, the first planned point and the second planned point being positioned so as to be included in the radiotherapy target region, and estimate a sighting point of the Bragg peak of a particle beam applied by the gantry based on a predetermined anatomical region inside a body of the subject specified by the ultrasonic image and an actual range of the particle beam applied by the gantry; and display configured to display the ultrasonic image so as to indicate the first planned point and the sighting point.

17. A particle beam radiotherapy system, comprising:

a gantry configured to apply particle beams to a subject;

an ultrasonic diagnostic apparatus configured to scan the subject with ultrasonic waves via an ultrasonic probe, and acquire an ultrasonic image concerning a radiotherapy target region of the subject;

processing circuitry configured to specify a first planned point of a Bragg peak in the ultrasonic image, which anatomically coincides approximately with a second planned point of the Bragg peak determined using a radiotherapy planning apparatus, the first planned point and the second planned point being positioned so as to be included in the radiotherapy target region, and estimate a sighting point of the Bragg peak of a particle beam applied by the gantry based on information concerning a body surface position of the subject and an actual range of the particle beam applied by the gantry; and control circuitry configured to switch between irradiation and a stoppage of the irradiation of the particle beam by the gantry based on a comparison between an actual range of the particle beam applied by the gantry and an ideal range from a body surface region to the first planned point.

* * * * *